(12) United States Patent
Giordanetto et al.

(10) Patent No.: US 7,723,331 B2
(45) Date of Patent: May 25, 2010

(54) THIENOPYRIMIDINE COMPOUNDS AND USES THEREOF

(75) Inventors: Fabrizio Giordanetto, Mölndal (SE); Tord Inghardt, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/840,382

(22) Filed: Aug. 17, 2007

(65) Prior Publication Data

US 2008/0051405 A1    Feb. 28, 2008

Related U.S. Application Data

(60) Provisional application No. 60/870,914, filed on Dec. 20, 2006, provisional application No. 60/838,762, filed on Aug. 18, 2006.

(51) Int. Cl.
| | | |
|---|---|---|
| *C07D 495/04* | (2006.01) | |
| *C07D 413/14* | (2006.01) | |
| *A61K 31/5355* | (2006.01) | |
| *A61K 31/519* | (2006.01) | |
| *A61P 3/04* | (2006.01) | |
| *A61P 25/18* | (2006.01) | |
| *A61P 25/22* | (2006.01) | |
| *A61P 25/28* | (2006.01) | |

(52) U.S. Cl. .............. 514/234.2; 514/260.1; 544/278; 544/117; 544/235

(58) Field of Classification Search ............. 544/278, 544/117, 238; 514/252.02, 252.1, 258.1, 514/230.8, 234.2, 260.1
See application file for complete search history.

(56) References Cited

FOREIGN PATENT DOCUMENTS

| WO | 03/033476 | 4/2003 |
|---|---|---|
| WO | 2004/092181 | 10/2004 |
| WO | 2005/042541 | 5/2005 |
| WO | 2005/103039 | 11/2005 |
| WO | 2006/118320 | 9/2006 |

OTHER PUBLICATIONS

Ahnaou, et al., Europ. J. Pharm., vol. 579, # 1-3, Jan. 28, 2008, 177-188.*
Ghoussaini, et al., J. Clin. Endocrin. & Metab., 2007, vol. 92, No. 11, 4403-4409.*
Duncan, et al., Alcoholism: Clin. & Experim. Res., 29(6):958-964, Jun. 2005.*
Chaki, et al., CNS Drug Reviews, vol. 11, No. 4, 341-352, 2005.*
Bjursell, et al., Diabetes 55:725-733, 2006.*
Hubbard, Newsmax.com, Oct. 20, 2008, http://www.newsmax.com/health/women_heart_anxiety/2008/10/20/142110.html, downloaded Jan. 24, 2009.*
Kym, et al., Current Topics in Med. Chem., vol. 7, # 15, Aug. 2007, pp. 1471-1488(18).*
Judd, et al., Current Topics in Med. Chem., vol. 8, # 13, Sep. 2008, pp. 1152-1157.*
Gehlert, et al., Neuropeptides, vol. 40, # 6, Dec. 2006, 428-429.*
Notice of Co-Pending Applications.
Hertzog et al., "The discovery and optimization of pyrimidinone-containing MCH R1 antagonists," Bioorganic & Medicinal Chemistry Letters (2006) 16(19):4723-4727.
Warshakoon et al., "Design and synthesis of substituted quinolines as novel and selective melanin concentrating hormone antagonists as anti-obesity agents," Bioorganic & Medicinal Chemistry Letters (2006) 16(19):5207-5211.
Mendez-Andino et al., "MCH-R1 antagonists: what is keeping most research programs away from the clinic?," Drug Discovery Today (2007) 12(21-22):972-979.
Nonfinal Office Action dated Jan. 9, 2009 received in copending U.S. Appl. No. 11/995,570.
Notice of Allowance dated Jul. 16, 2009 received in copending U.S. Appl. No. 11/995,570.

* cited by examiner

*Primary Examiner*—James O Wilson
*Assistant Examiner*—Cecilia M Jaisle
(74) *Attorney, Agent, or Firm*—Pepper Hamilton LLP

(57) ABSTRACT

The present invention provides compounds of the class of thienopyrimidines, processes for preparing such compounds, their use in the treatment of obesity, psychiatric disorders, cognitive disorders, memory disorders, schizophrenia, epilepsy, and related conditions, type II diabetes, Metabolic syndrome and neurological disorders such as dementia, multiple sclerosis, Parkinson's disease, Huntington's chorea, Alzheimer's disease, and pain related disorders, and to pharmaceutical compositions containing them.

13 Claims, No Drawings

THIENOPYRIMIDINE COMPOUNDS AND USES THEREOF

CROSS-REFERENCE TO RELATED APPLICATIONS

This application claims priority to U.S. provisional application Ser. No. 60/870,914 filed Dec. 20, 2006, and claims priority to U.S. provisional application Ser. No. 60/838,762 filed Aug. 18, 2006, each which is incorporated herein by reference in its entirety.

FIELD OF THE INVENTION

The present invention relates to certain compounds of formula I, to their use in the treatment of obesity, psychiatric and neurological disorders, and to pharmaceutical compositions containing them.

BACKGROUND OF THE INVENTION

Melanin concentrating hormone (MCH) is a cyclic peptide that was first isolated from fish over 15 years ago. In mammals, MCH gene expression is localised to the ventral aspect of the zona inserta and the lateral hypothalamic area (Breton et al., Molecular and Cellular Neurosciences, 1993, vol. 4, 271-284). The latter region of the brain is associated with the control of behaviours such as eating and drinking, with arousal and with motor activity (Baker, B., Trends Endocrinol. Metab., 1994, 5, 120-126). Although the biological activity in mammals has not been fully defined, recent work has indicated that MCH promotes eating and weight gain (U.S. Pat. No. 5,849,708). Thus, MCH and its agonists have been proposed as treatments for anorexia nervosa and weight loss due to AIDS, renal disease, or chemotherapy. Similarly, antagonists of MCH can be used as a treatment for obesity and other disorders characterised by compulsive eating and excessive body weight. MCH projections are found throughout the brain, including the spinal cord, an area important in processing nociception, indicates that agents acting through MCHr1, such as compounds of formula I, will be useful in treating pain.

Two receptors for MCH, MCH receptor 1 (MCHr1) (Shimomura et al., Biochem Biophys Res Commun, 1999, 261, 622-6) and MCH receptor 2 (MCHr2) (Hilo et al., J Biol. Chem., 2001, 276, 20125-9) have been identified in humans, while only one (MCHr1) is present in rodent species (Tan et al., Genomics, 2002, 79, 785-92). In mice lacking MCHr1, there is no increased feeding response to MCH, and a lean phenotype is seen, suggesting that this receptor is responsible for mediating the feeding effect of MCH (Marsh et al., Proc. Natl. Acad. Sci. USA, 2002, 99, 3240-5). In addition, MCHr1 antagonists have been demonstrated to block the feeding effects of MCH (Takekawa et al., Eur. J. Pharmacol., 2002, 438, 129-35), and to reduce body weight & adiposity in diet-induced obese rats (Borowsky et al., Nature Med., 2002, 8, 825-30). The conservation of distribution and sequence of MCHr1 suggest a similar role for this receptor in man and rodent species. Hence, MCHr1 antagonists have been proposed as a treatment for obesity and other disorders characterised by excessive eating and body weight. Also, it has been reported that MCHr1 antagonists exhibit antidepressant and anxiolytic-like effects in rodent tests, suggesting a role for MCHr1 in depression and anxiety as well as in other psychiatric disorders (reviewed in Hervieu, G. J., Expert Opin. Ther. Targets, 2006, 10, 211-229).

WO 2003/033476, WO 2004/092181 and WO 2005/042541 discloses 3-phenyl-thieno-pyrimid-4-one derivatives as MCHr1 antagonists for the treatment of obesity and other diseases.

WO 2005/103039 discloses e.g. 3-(pyridin-3-yl)-thienopyrimid-4-one, 6-(pyrid-3-yl)-thienopyridazin-7-one and 6-(pyridin-3-yl)-thienopyran-7-one derivatives as MCHr1 antagonists for treatment of obesity, anxiety, depression and other diseases.

WO 2005/047293 discloses 3-(pyrrolidin-3-yl)-thienopyrimid-4-one derivatives as MCHr1 antagonists for treatment of obesity, anxiety and depression.

Substituted quinoline analogs, containing a chlorophenyl substituted thienopyrimidinone ring system, are presented as MCHr1 antagonists in Warshakoon, N. C. et al., Bioorganic & Medicinal Chemistry Letters, 2006, doi:10.106/j.bmcl.2006.07.006.

Pyrimidine fused bicyclic metalloproteinase inhibitors are disclosed in WO 2004/014916.

Thienopyrimidin-4-one derivatives are disclosed as angiotensin II receptor blockers in WO 93/03040.

Thienopyrimidin-4-one derivatives are disclosed as MCHr1 antagonists for the treatment of obesity in WO2006/118320.

There is an unmet need for MCHr1 antagonists that are more efficacious, more selective (e.g. vs ion channels), more chemically stable, more soluble, more bioavailable and which produce less side effects than known compounds in this field.

SUMMARY OF THE INVENTION

It is an object of the present invention to provide compounds, which are useful in treating obesity and related disorders, psychiatric disorders, neurological disorders and pain. This object has been reached in that compounds of formula I have been provided for use as a MCHr1 antagonist.

According to another aspect of the invention, a pharmaceutical formulation is provided comprising a compound of formula I, and a pharmaceutically acceptable adjuvant, diluent or carrier.

According to a further aspect of the invention, the use of a compound of formula I is provided, in the preparation of a medicament for the treatment or prophylaxis of conditions associated with obesity.

According to yet another aspect of the invention, a method is provided of treating obesity, psychiatric disorders, anxiety, anxio-depressive disorders, depression, bipolar disorder, ADHD, cognitive disorders, memory disorders, schizophrenia, epilepsy, and related conditions, and neurological disorders and pain related disorders, comprising administering a pharmacologically effective amount of a compound of Formula I to a patient in need thereof.

According to a further aspect of the invention, a method is provided of treating obesity, type II diabetes, Metabolic syndrome and prevention of type II diabetes comprising administering a pharmacologically effective amount of a compound of formula I to a patient in need thereof.

In particular, the present invention provides compounds of formula I

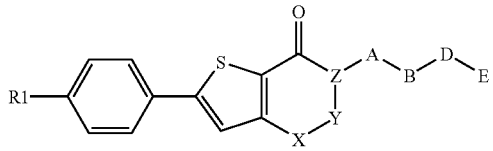

wherein: X—Y—Z represents N=CH—N or CH—N=N; R¹ represents Cl, Br, F, $C_{1-3}$ alkyl (optionally substituted with one or more F), or $C_{1-3}$ alkoxy (optionally substituted with one or more F); A represents a group —C(R²)₂-[(CR³)₂]$_m$—, wherein R² and R³, independently, represent H or $C_{1-3}$ alkyl, and wherein m is 0 or 1; B represents phenyl, pyridinyl, pyrimidinyl, pyridazinyl, pyrazinyl, thiazolyl, or thiophenyl, each optionally substituted by one or more cyano, halo, $C_{1-3}$ alkyl (optionally substituted with OH, OMe and/or with one or more of F), or $C_{1-3}$ alkoxy (optionally substituted with one or more F or with OMe); D represents a bond, —(CH₂)$_n$—, where n is 1 or 2, or —O(CH₂)$_p$—, where p is 0 to 2; E represents one of the following:

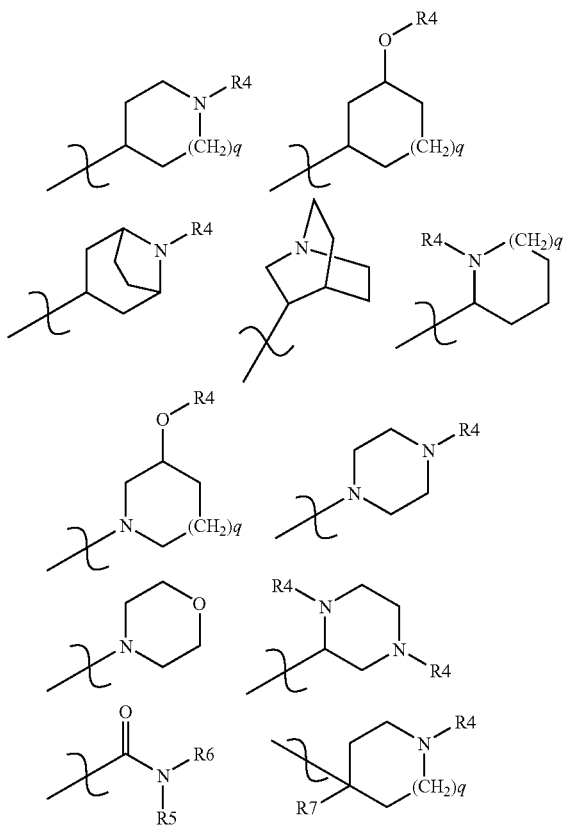

wherein: R⁴ represents H or $C_{1-5}$ alkyl, substituted with one or more F, OH, OCHF₂ or OCF₃; R⁵ and R⁶, independently, represent H, $C_{1-5}$ alkyl, or $C_{3-6}$ cycloalkyl, or R⁵ and R⁶, together with the nitrogen to which they are attached, form a 5 or 6 membered ring optionally containing another nitrogen or oxygen atom; q is 0 or 1; and R⁷ represents $C_{1-3}$ alkyl optionally substituted with one or more OH; or a tautomer, optical isomer, or racemate thereof, as well as a pharmaceutically acceptable salt thereof.

In some embodiments, X—Y—Z represents CH—N=N. In some embodiments, X—Y—Z represents N=CH—N. In any of the foregoing embodiments, R¹ is C₁ or CF₃. In any of the foregoing embodiments, A is CH₂. In any of the foregoing embodiments, B is 2,6-pyridinyl. In any of the foregoing embodiments, B is phenyl. In any of the foregoing embodiments, E is

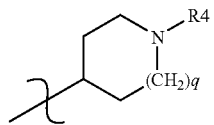

and R⁴ represents H or methyl, and q is 1. In any of the foregoing embodiments, B represents phenyl or pyridinyl, and D represents —O(CH₂)$_p$—, where p is 0 to 1. In any of the foregoing embodiments, D is —O—. In any of the foregoing embodiments, D is —O— and E is

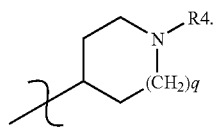

In some embodiments, X—Y—Z represents N=CH—N or CH—N=N; R¹ represents Cl, $C_{1-3}$ alkyl (optionally substituted with one or more F), or methoxy (optionally substituted with one or more F); A represents CH₂; B represents phenyl, pyridinyl, pyrimidinyl, pyridazinyl, pyrazinyl, thiazolyl, or thiophenyl, each optionally substituted by a cyano, a halo, or a hydroxymethyl; D represents —O(CH₂)$_p$—, where p is 0 to 1; and E represents:

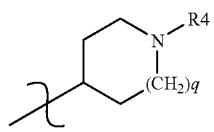

wherein R⁴ represents H or methyl.

In some embodiments, the invention provides one or more of the following compounds: 6-(4-chlorophenyl)-3-(3-{[(3-endo)-8-methyl-8-azabicyclo[3.2.1]oct-3-yl]oxy}benzyl)thieno[3,2-d]pyrimidin-4(3H)-one; 6-(4-chlorophenyl)-3-{3-[(1-methylpiperidin-4-yl)oxy]benzyl}thieno[3,2-d]pyrimidin-4(3H)-one; 4-{2-[6-(4-chlorophenyl)-4-oxothieno[3,2-d]pyrimidin-3(4H)-yl]ethyl}-N,N-diethylbenzamide; 6-(4-chlorophenyl)-3-[3-(4-methylpiperazin-1-yl)benzyl]thieno[3,2-d]pyrimidin-4(3H)-one; 6-(4-chlorophenyl)-3-{3-[(4-methylpiperazin-1-yl)methyl]benzyl}thieno[3,2-d]pyrimidin-4(3H)-one; 6-(4-chlorophenyl)-3-[3-(2-morpholin-4-yl-ethoxy)benzyl]thieno[3,2-d]pyrimidin-4(3H)-one; 6-(4-chlorophenyl)-3-(3-{[(3-exo)-8-methyl-8-azabicyclo[3.2.1]oct-3-yl]oxy}benzyl)thieno[3,2-d]pyrimidin-4(3H)-one; 2-(4-chlorophenyl)-6-{3-[(1-methylpiperidin-4-yl)oxy]benzyl}thieno[2,3-d]pyridazin-7(6H)-one; 6-{3-[(1- methylpiperidin-4-yl)oxy]benzyl}-2-[4-(trifluoromethyl) phenyl]thieno[2,3-d]pyridazin-7(6H)-one; 6-(4-chlorophenyl)-3-{3-[(3R)-3-hydroxypyrrolidin-1-yl]benzyl}thieno[3,2-d]pyrimidin-4(3H)-one; 6-(4-chlorophenyl)-3-({6-[(1-methylpiperidin-4-yl)oxy]pyridin-2-yl}methyl)thieno[3,2-d]pyrimidin-4(3H)-one; 6-(4-chlorophenyl)-3-{3-[(1-methylpiperidin-3-yl)oxy]benzyl}thieno[3,2-d]pyrimidin-4(3H)-one; 6-(4-chlorophenyl)-3-{3-[(1-methylpiperidin-4-yl)methoxy]benzyl}thieno[3,2-d]pyrimidin-4(3H)-one; 6-(4-chlorophenyl)-3-[3-(piperidin-4-yloxy)benzyl]thieno[3,2-d]pyrimidin-4(3H)-one; 6-(4-chlorophenyl)-3-({2-[(1-methylpiperidin-4-yl)oxy]pyridin-4-yl}methyl)thieno[3,2-d]pyrimidin-4(3H)-one; 6-(4-chlorophenyl)-3-{3-[(1,4-dimethylpiperazin-2-yl)methoxy]benzyl}thieno[3,2-d]pyrimidin-4(3H)-one; 6-(4-chlorophenyl)-3-{3-[(1-methylpyrrolidin-3-yl)methoxy]benzyl}thieno[3,2-d]pyrimidin-4(3H)-one; 3-{3-[(3R)-1-azabicyclo[2.2.2]oct-3-yloxy]benzyl}-6-(4-chlorophenyl)thieno[3,2-d]pyrimidin-4(3H)-one; 6-(4-chlorophenyl)-3-{3-[(1-isopropylpiperidin-4-yl)oxy]benzyl}thieno[3,2-d]pyrimidin-4(3H)-one; 6-(4-chlorophenyl)-3-{3-[(1,3-dimethylpiperidin-3-yl)methoxy]benzyl}thieno[3,2-d]pyrimidin-4(3H)-one; 2-(4-chlorophenyl)-6-({6-[(1-methylpiperidin-4-yl)oxy]pyridin-2-yl}methyl)thieno[2,3-d]pyridazin-7(6H)-one; 2-(4-methoxyphenyl)-6-[(6-{[(2S)-1-methylpiperidin-2-yl]methoxy}pyridin-2-yl)methyl]thieno[2,3-d]pyridazin-7(6H)-one; 6-(4-chlorophenyl)-3-[(6-{[1-(2-hydroxyethyl)piperidin-4-yl]oxy}pyridin-2-yl)methyl]thieno[3,2-d]pyrimidin-4(3H)-one; 6-(4-chlorophenyl)-3-(3-{[(2S)-1-methylpyrrolidin-2-yl]methoxy}benzyl)thieno[3,2-d]pyrimidin-4(3H)-one; and 2-(4-chlorophenyl)-6-[(6-{[(2R)-1-methylpyrrolidin-2-yl]methoxy}pyridin-2-yl)methyl]thieno[2,3-d]pyridazin-7(6H)-one; as well as a tautomer, optical isomer, or racemate thereof, as well as a pharmaceutically acceptable salt thereof.

The present invention also provides pharmaceutical formulations comprising any of the foregoing compounds and a pharmaceutically acceptable adjuvant, diluent, or carrier.

The present invention also provides methods of treating obesity, a psychiatric disorder, anxiety, an anxio-depressive disorder, depression, bipolar disorder, ADHD, a cognitive disorder, a memory disorder, schizophrenia, epilepsy or a related condition, a neurological disorder, or a pain related disorder, comprising administering a pharmacologically effective amount of any of the foregoing compounds to a patient in need thereof.

The present invention also provides methods of treating obesity, type II diabetes, or metabolic syndrome, or preventing type II diabetes, comprising administering a pharmacologically effective amount of any of the foregoing compounds to a patient in need thereof.

DESCRIPTION OF EMBODIMENTS

The invention relates to compounds of the general formula I

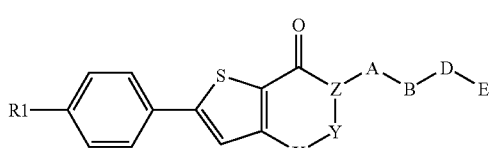

wherein:

X—Y—Z represents N=CH—N or CH—N=N;

$R^1$ represents Cl, Br, F, $C_{1-3}$ alkyl (optionally substituted with one or more F), or $C_{1-3}$ alkoxy (optionally substituted with one or more F);

A represents a group —$C(R^2)_2$-$[(CR^3)_2]_m$—, wherein $R^2$ and $R^3$, independently, represent H or $C_{1-3}$ alkyl, and wherein m is 0 or 1;

B represents phenyl, pyridinyl, pyrimidinyl, pyridazinyl, pyrazinyl, thiazolyl, or thiophenyl, each optionally substituted by one or more cyano, halo, $C_{1-3}$ alkyl (optionally substituted with OH, OMe and/or with one or more of F), or $C_{1-3}$ alkoxy (optionally substituted with one or more F or with OMe);

D represents a bond, —$(CH_2)_n$—, where n is 1 or 2, or —$O(CH_2)_p$—, where p is 0 to 2;

E represents one of the following:

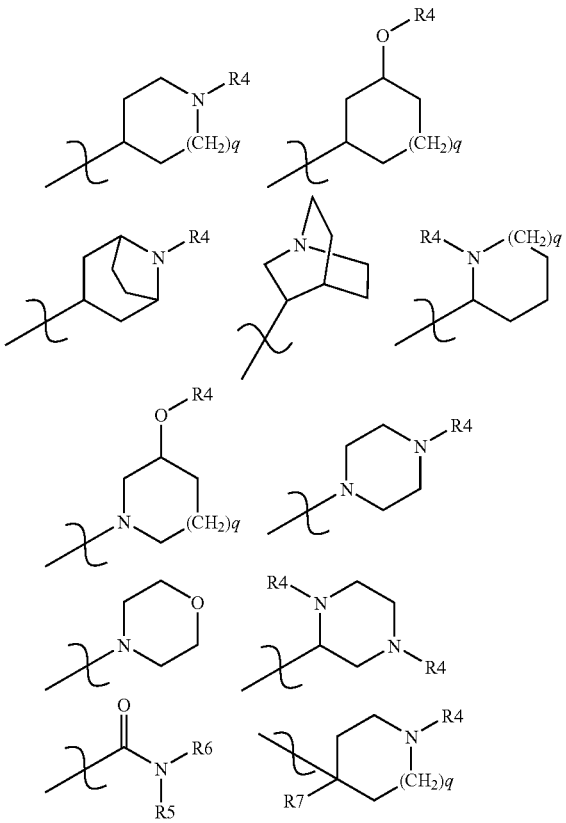

wherein:

$R^4$ represents H or $C_{1-5}$ alkyl, substituted with one or more F, OH, $OCHF_2$, or $OCF_3$;

$R^5$ and $R^6$, independently, represent H, $C_{1-5}$ alkyl or $C_{3-6}$ cycloalkyl, or $R^5$ and $R^6$, together with the nitrogen to which they are attached, form a 5 or 6 membered ring optionally containing another nitrogen or oxygen atom;

q is 0 or 1; and $R^7$ represents $C_{1-3}$ alkyl optionally substituted with one or more OH;

and a tautomer, optical isomer, or racemate thereof, as well as a pharmaceutically acceptable salt thereof.

Particular groups now follow in which some of A, B, D, E, X, Y, Z, n, m, p, q, $R^1$, $R^2$, $R^3$, $R^4 R^5$ and $R^6$ in compounds of formula I are further defined. It will be understood that such group definitions may be used where appropriate with any of the other group definitions, claims or embodiments defined hereinbefore or hereinafter.

In one particular group of compounds of formula I, X—Y—Z represents CH—N=N. In another particular group of compounds of formula I, X—Y—Z represents N=CH—N.

In another particular group of compounds of formula I, $R^1$ is Cl or $CF_3$.

In another particular group of compounds of formula I, A is $CH_2$.

In another particular group of compounds of formula I, B is phenyl.

In another particular group of compounds of formula I, B is pyridinyl and in yet another group B is 2,6-pyridinyl.

In yet another group of compounds of formula I, E is

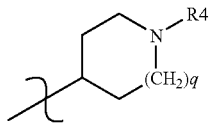

and $R^4$ represents H or methyl and q is 1.

In one group of Formula I, D represents —O(CH$_2$)$_p$— where p is 0 to 1.

In another particular group of compounds of formula I, B represents phenyl or pyridinyl, and D represents —O (CH$_2$)$_p$— where p is 0 to 1.

In another particular group of compounds of formula I, D is —O—.

In another particular group of formula I, D is —O— and E is

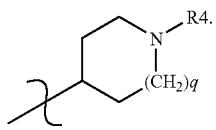

In yet one particular group, X—Y—Z represents N=CH—N or CH—N=N; $R^1$ represents Cl, $C_{1-3}$ alkyl (optionally substituted with one or more F), or methoxy (optionally substituted with one or more F); A represents $CH_2$; B represents phenyl, pyridinyl, pyrimidinyl, pyridazinyl, pyrazinyl, thiazolyl, or thiophenyl, each optionally substituted by a cyano, or a halo or a hydroxymethyl; and E represents:

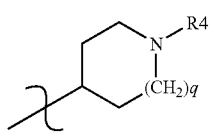

wherein $R^4$ represents H or methyl.

In one group of compounds of Formula I, $R^4$ represents H or $C_{1-5}$ alkyl.

In another group of compounds of Formula I, $R^4$ represents H or $C_{1-5}$ alkyl substituted with one or more F, OH, OCHF$_2$ or OCF$_3$.

In another group of compounds of Formula I, E represents

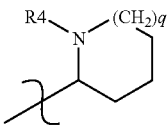 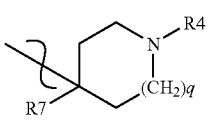

wherein $R^4$ represents H or $C_{1-5}$ alkyl, substituted with one or more F, OH, OCHF$_2$ or OCF$_3$, and $R^7$ represents $C_{1-3}$ alkyl optionally substituted with one or more OH.

In one group of compounds of Formula I, E represents one of the following

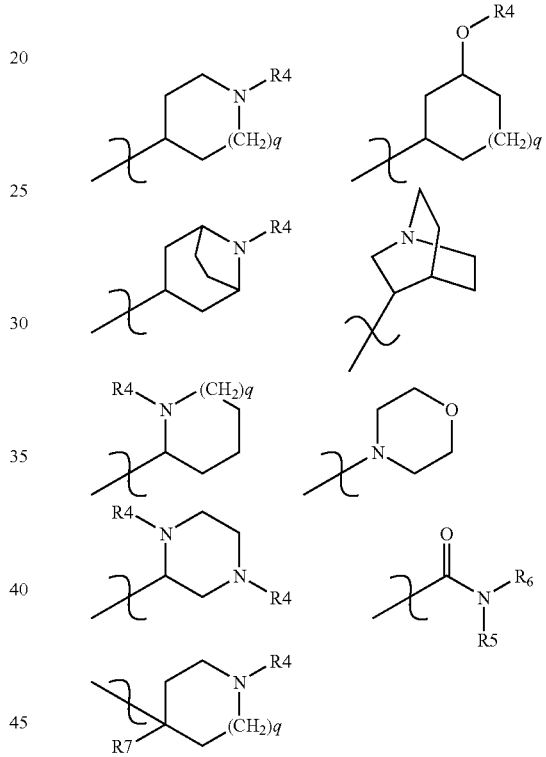

The term "pharmaceutically acceptable salt" refers to pharmaceutically acceptable acid addition salt. A suitable pharmaceutically acceptable salt of a compound of Formula I is, for example, an acid-addition salt of a compound of Formula I which is sufficiently basic, for example an acid-addition salt with an inorganic or organic acid such as: (1S)-(+)-10-camphorsulfonic acid; cyclohexylsulfamic acid; phosphoric acid; dimethylphosphoric acid; p-toluenesulfonic acid; L-lysine; L-lysine hydrochloride; saccharinic acid; methanesulfonic acid; hydrobromic acid; hydrochloric acid; sulphuric acid; 1,2-ethanedisulfonic acid; (+/−)-camphorsulfonic acid; ethanesulfonic acid; nitric acid; p-xylenesulfonic acid; 2-mesitylenesulfonic acid; 1,5-naphthalenedisulfonic acid; 1-naphthalenesulfonic acid; 2-naphthalenesulfonic acid; benzenesulfonic acid; maleic acid; D-glutamic acid; L-glutamic acid; D,L-glutamic acid; L-arginine; glycine; salicylic acid; tartaric acid; fumaric acid; citric acid; L-(−)-malic acid; D,L-malic acid; and D-gluconic acid.

Throughout the specification and the appended claims, a given chemical formula or name shall encompass all tautomers, all stereo and optical isomers and racemates thereof as well as mixtures in different proportions of the separate enantiomers, where such isomers and enantiomers exist, as well as pharmaceutically acceptable salts thereof. Isomers may be separated using conventional techniques, e.g. chromatography or fractional crystallisation. The enantiomers may be isolated by separation of racemate for example by fractional crystallisation, resolution or HPLC. The diastereomers may be isolated by separation of isomer mixtures for instance by fractional crystallisation, HPLC or flash chromatography. Alternatively the stereoisomers may be made by chiral synthesis from chiral starting materials under conditions, which will not cause racemisation or epimerisation, or by derivatisation, with a chiral reagent. All stereoisomers are included within the scope of the invention.

The following definitions shall apply throughout the specification and the appended claims.

Unless otherwise stated or indicated, the term "alkyl" denotes either a straight chain or a branched alkyl group. Examples of alkyl include, but are not limited to, methyl, ethyl, n-propyl, isopropyl, cyclopropyl, n-butyl, iso-butyl, sec-butyl and t-butyl. Preferred alkyl groups are methyl, ethyl, propyl, isopropyl and tertiary butyl.

Unless otherwise stated or indicated, the term "alkoxy" denotes a group O-alkyl, wherein alkyl is as defined above.

Specific compounds of the invention include, but are not limited to: 6-(4-chlorophenyl)-3-(3-{[(3-endo)-8-methyl-8-azabicyclo[3.2.1]oct-3-yl]oxy}benzyl)thieno[3,2-d]pyrimidin-4(3H)-one, 6-(4-chlorophenyl)-3-{3-[(1-methylpiperidin-4-yl)oxy]benzyl}thieno[3,2-d]pyrimidin-4(3H)-one, 4-{2-[6-(4-chlorophenyl)-4-oxothieno[3,2-d]pyrimidin-3(4H)-yl]ethyl}-N,N-diethylbenzamide, 6-(4-chlorophenyl)-3-[3-(4-methylpiperazin-1-yl)benzyl]thieno[3,2-d]pyrimidin-4(3H)-one, 6-(4-chlorophenyl)-3-{3-[(4-methylpiperazin-1-yl)methyl]benzyl}thieno[3,2-d]pyrimidin-4(3H)-one, 6-(4-chlorophenyl)-3-[3-(2-morpholin-4-yl-ethoxy)benzyl]thieno[3,2-d]pyrimidin-4(3H)-one, 6-(4-chlorophenyl)-3-(3-{[(3-exo)-8-methyl-8-azabicyclo[3.2.1]oct-3-yl]oxy}benzyl)thieno[3,2-d]pyrimidin-4(3H)-one, 2-(4-chlorophenyl)-6-{3-[(1-methylpiperidin-4-yl)oxy]benzyl}thieno[2,3-d]pyridazin-7(6H)-one, 6-{3-[(1-methylpiperidin-4-yl)oxy]benzyl}-2-[4-(trifluoromethyl)phenyl]thieno[2,3-d]pyridazin-7(6H)-one, 6-(4-chlorophenyl)-3-{3-[(3R)-3-hydroxypyrrolidin-1-yl]benzyl}thieno[3,2-d]pyrimidin-4(3H)-one, 6-(4-chlorophenyl)-3-({6-[(1-methylpiperidin-4-yl)oxy]pyridin-2-yl}methyl)thieno[3,2-d]pyrimidin-4(3H)-one, 6-(4-chlorophenyl)-3-{3-[(1-methylpiperidin-3-yl)oxy]benzyl}thieno[3,2-d]pyrimidin-4(3H)-one, 6-(4-chlorophenyl)-3-{3-[(1-methylpiperidin-4-yl)methoxy]benzyl}thieno[3,2-d]pyrimidin-4(3H)-one, 6-(4-chlorophenyl)-3-[3-(piperidin-4-yloxy)benzyl]thieno[3,2-d]pyrimidin-4(3H)-one, 6-(4-chlorophenyl)-3-({2-[(1-methylpiperidin-4-yl)oxy]pyridin-4-yl}methyl)thieno[3,2-d]pyrimidin-4(3H)-one, 6-(4-chlorophenyl)-3-{3-[(1,4-dimethylpiperazin-2-yl)methoxy]benzyl}thieno[3,2-d]pyrimidin-4(3H)-one, 6-(4-chlorophenyl)-3-{3-[(1-methylpyrrolidin-3-yl)methoxy]benzyl}thieno[3,2-d]pyrimidin-4(3H)-one, 3-{3-[(3R)-1-azabicyclo[2.2.2]oct-3-yloxy]benzyl}-6-(4-chlorophenyl)thieno[3,2-d]pyrimidin-4(3H)-one, 6-(4-chlorophenyl)-3-{3-[(1-isopropylpiperidin-4-yl)oxy]benzyl}thieno[3,2-d]pyrimidin-4(3H)-one, 6-(4-chlorophenyl)-3-{3-[(1,3-dimethylpiperidin-3-yl)methoxy]benzyl}thieno[3,2-d]pyrimidin-4(3H)-one, 2-(4-chlorophenyl)-6-({6-[(1-methylpiperidin-4-yl)oxy]pyridin-2-yl}methyl)thieno[2,3-d]pyridazin-7(6H)-one, 2-(4-methoxyphenyl)-6-[(6-{[(2S)-1-methylpiperidin-2-yl]methoxy}pyridin-2-yl)methyl]thieno[2,3-d]pyridazin-7(6H)-one, 6-(4-chlorophenyl)-3-[(6-{[1-(2-hydroxyethyl)piperidin-4-yl]oxy}pyridin-2-yl)methyl]thieno[3,2-d]pyrimidin-4(3H)-one, 6-(4-chlorophenyl)-3-(3-{[(2S)-1-methylpyrrolidin-2-yl]methoxy}benzyl)thieno[3,2-d]pyrimidin-4(3H)-one, and 2-(4-chlorophenyl)-6-[(6-{[(2R)-1-methylpyrrolidin-2-yl]methoxy}pyridin-2-yl)methyl]thieno[2,3-d]pyridazin-7(6H)-one, and tautomers, optical isomers and racemates thereof as well as pharmaceutically acceptable salts thereof.

Methods of Preparation

The compounds of the invention may be prepared as outlined below according to any of the following methods. However, the invention is not limited to these methods, the compounds may also be prepared as described for structurally related compounds in the prior art.

Compounds of formula I, in which X—Y represent N═C and in which A, B, D, E and R$^1$ are as hereinbefore defined, may for example be prepared by reacting a compound of formula II with an amine of formula III, in analogy with methodology described in WO 2003/033476. Preferably, this reaction is carried out at 80-150° C. (e.g. in a microwave reactor) using EtOH, MeOH or phenol as solvent.

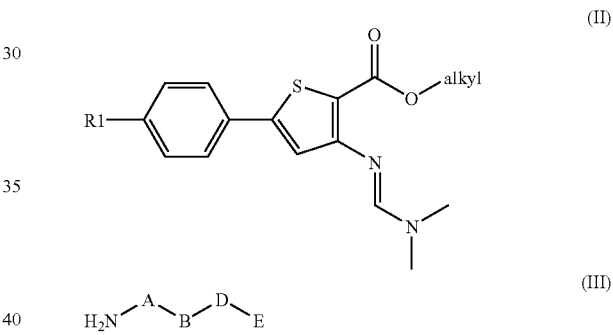

Alternatively, compounds of formula I may be prepared via a Suzuki or a Stille coupling reaction of a compound of formula IV with a compound of formula V in which T represents B(OH)$_2$ or Sn(alkyl)$_3$ and X represents a suitable leaving group such as I, Br or triflate.

Compounds of formula I, in which X—Y represents C═N and in which A, B, D, E and R$^1$ are as hereinbefore defined, may for example be prepared by condensing, in refluxing EtOH followed by heating (of the intermediate hydrazone) in HOAc, a compound of formula VI with an aryl hydrazine VII, in analogy with methodologies described in Baraldi et al., Nucleosides & Nucleotides, 1998, 17, 2165-73 and in Marquet et al., Tetrahedron, 1973, 29, 435-39

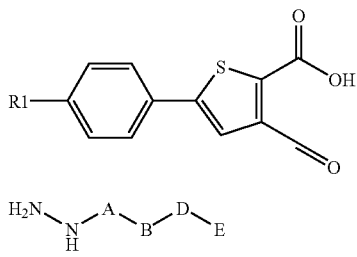

Alternatively, compounds of formula I, in which X—Y represents C═N and in which A, B, D, E and R¹ are as hereinbefore defined, may be prepared by N-alkylation of compounds of formula VIII with compounds of formula IX, wherein Y represents a suitable leaving group such as mesylate, tosylate, Cl, Br or I, at a temperature in the range of 0° C. to 100° C., preferably in the range of 0° C. to 50° C. in an aprotic solvent, for example DMF in the presence of a strong base for example NaH.

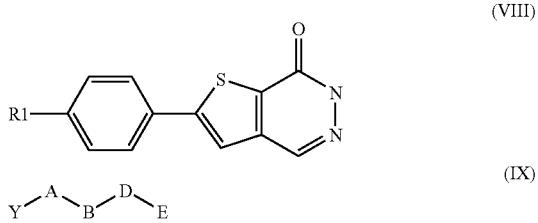

Compounds of formulae II-IX are either commercially available, known in the literature or can readily be prepared by methods known to those skilled in the art, e.g. as described hereinafter in the Experimental section.

Persons skilled in the art will appreciate that in some cases, in order to obtain compounds of the invention, functional groups (e.g. hydroxy, amino, aldehyde or carboxylic acids groups) in compounds II-IX, as well as in their synthetic precursors, may require protection prior to the reactions described above. Amine protecting groups are known to those skilled in the art, for example the ally, benzyl, t-Boc, or Cbz groups. Aromatic amino groups may also be masked as nitro groups during the reaction sequence. Hydroxy protecting groups are known to those skilled in the art, for example the t-butyl ether, TBDMS ether or THP, MEM or similar acetal type protecting groups. Phenolic hydroxy groups may also be temporarily protected as a mesylate esters. Aldehyde protecting groups comprise acetals, e.g. diethyl acetals. Carboxylic acid protecting groups are for example benzyl, t-butyl, ethyl or methyl esters.

The compounds of the invention may be isolated from their reaction mixtures using conventional techniques. Stereoisomers may be separated using conventional techniques, e.g. chromatography or fractional crystallisation. Enantiomers may be isolated by separation of racemate for example by fractional crystallisation, resolution or HPLC. The diastereomers may be isolated by separation of isomer mixtures for instance by fractional crystallisation, HPLC or flash chromatography. Alternatively the stereoisomers may be made by chiral synthesis from chiral starting materials under conditions which will not cause racemisation or epimerisation, or by derivatisation, with a chiral reagent.

Persons skilled in the art will appreciate that, in order to obtain compounds of the invention in an alternative and in some occasions, more convenient manner, the individual process steps mentioned hereinbefore may be performed in a different order, and/or the individual reactions may be performed at a different stage in the overall route (i.e. chemical transformations may be performed upon different intermediates to those associated hereinbefore with a particular reaction). The scheme below serves to illustrate the general synthetic methodology (in this case leading to the title compound of Example 8):

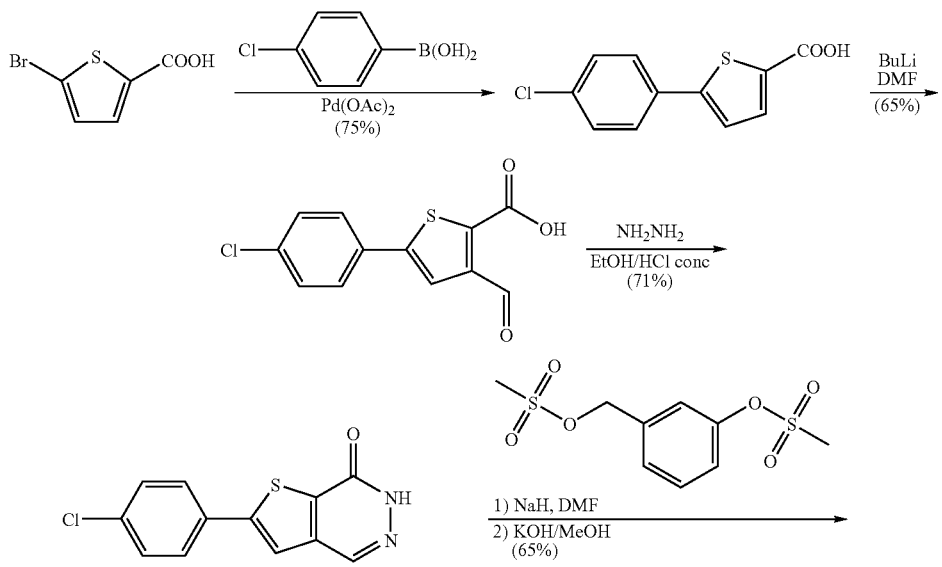

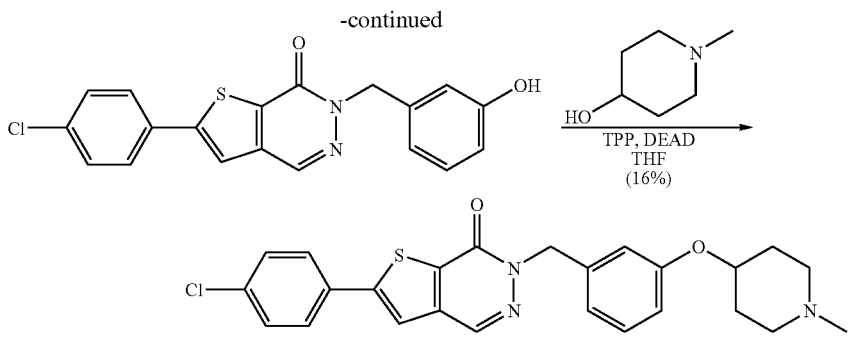

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient either as a free base, or a pharmaceutically acceptable inorganic or organic addition salt, in a pharmaceutically acceptable dosage form. Depending upon the disorder and patient to be treated and the route of administration, the compositions may be administered at varying doses.

Suitable daily doses of the compounds of the invention in the therapeutic treatment of humans are about 0.001-10 mg/kg body weight, preferably 0.01-3 mg/kg body weight.

In one aspect oral formulations are provided, in particular tablets or capsules which may be formulated by methods known to those skilled in the art to provide doses of the active compound in the range of 0.5 mg to 500 mg for example 1 mg, 3 mg, 5 mg, 10 mg, 25 mg, 50 mg, 100 mg and 250 mg.

According to a further aspect of the invention there is also provided a pharmaceutical formulation including any of the compounds of the invention, or pharmaceutically acceptable derivatives thereof, in admixture with pharmaceutically acceptable adjuvants, diluents and/or carriers.

The compounds of the invention may also be combined with other therapeutic agents, which are useful in the treatment of disorders associated with obesity, psychiatric disorders, type II diabetes, neurological disorders and pain.

Pharmacological Properties

The compounds of formula I are useful for the treatment of obesity, a psychiatric disorder such as a psychotic disorder, anxiety, an anxio-depressive disorder, depression, a cognitive disorder, a memory disorder, schizophrenia, epilepsy, and related conditions, and a neurological disorder such as dementia, multiple sclerosis, Raynaud's syndrome, Parkinson's disease, Huntington's chorea, and Alzheimer's disease. The compounds are also potentially useful for the treatment of immune, cardiovascular, reproductive, and endocrine disorders, and diseases related to the respiratory and gastrointestinal systems. The compounds are also potentially useful as agents for ceasing consumption of tobacco, treating nicotine dependence and/or treating nicotine withdrawal symptoms, reducing the craving for nicotine and as anti-smoking agents. The compounds may also eliminate the increase in weight that normally accompanies the cessation of smoking. The compounds are also potentially useful as agents for treating or preventing diarrhea.

The compounds are also potentially useful as agents for reducing the craving/relapse for an addictive substance that includes, but is not limited to, a psychomotor-active agent such as nicotine, alcohol, cocaine, amphetamines, opiates, benzodiazepines, or barbiturates. The compounds are also potentially useful as agents for treating drug addiction and/or drug abuse.

Accordingly, it is desirable to provide a compound and method of treatment which will be active in reducing craving for the abused substance, and which does not exacerbate the sympathetic response rate caused by the abused substance and which has favourable pharmacodynamic effects.

The compounds are also potentially useful as agents for treating a pain disorder, including, but not limited to, acute and chronic nociceptive, inflammatory and neuropathic pain and migraine.

In another aspect, the present invention provides a compound of formula I as claimed in any previous claim for use as a medicament.

In a further aspect, the present invention provides the use of a compound of formula I in the preparation of a medicament for the treatment or prophylaxis of obesity, a psychiatric disorder such as a psychotic disorder, anxiety, an anxio-depressive disorder, depression, bipolar disorder, ADHD, a cognitive disorder, a memory disorder, schizophrenia, epilepsy, and related conditions, a neurological disorder such as dementia, multiple sclerosis, Parkinson's disease, Huntington's chorea, and Alzheimer's disease, and a pain related disorder, including, but not limited to, acute and chronic nociceptive, inflammatory and neuropathic pain and migraine, comprising administering a pharmacologically effective amount of a compound of formula I to a patient in need thereof.

In a still further aspect the present invention provides methods of treating obesity, a psychiatric disorder such as a psychotic disorder, anxiety, an anxio-depressive disorder, depression, bipolar disorder, ADHD, a cognitive disorder, a memory disorder, schizophrenia, epilepsy, and related conditions, and a neurological disorder such as dementia, multiple sclerosis, Parkinson's disease, Huntington's chorea, and Alzheimer's disease, and a pain related disorder, including, but not limited to, acute and chronic nociceptive, inflammatory and neuropathic pain and migraine, comprising administering a pharmacologically effective amount of a compound of formula I to a patient in need thereof.

The compounds of the present invention are particularly suitable for the treatment of obesity.

In another aspect the present invention provides a method of treating obesity, type II diabetes, Metabolic syndrome and a method of preventing type II diabetes comprising administering a pharmacologically effective amount of a compound of formula I to a patient in need thereof.

Combination Therapy

The compounds of the invention may be combined with another therapeutic agent that is useful in the treatment of disorders associated with the development and progress of atherosclerosis such as hypertension, hyperlipidaemias, dyslipidaemias, diabetes, and/or obesity. For example, a compound of the present invention may be used in combination with a compound that affects thermogenesis, lipolysis, fat absorption, satiety, or gut motility. The compounds of the invention may be combined with another therapeutic agent that decreases the ratio of LDL:HDL or an agent that causes a decrease in circulating levels of LDL-cholesterol. In patients with diabetes mellitus the compounds of the invention may also be combined with therapeutic agents used to treat complications related to micro-angiopathies.

The compounds of the invention may be used alongside other therapies for the treatment of metabolic syndrome or type II diabetes and its associated complications; these include biguamide drugs, insulin (synthetic insulin analogues), oral antihyperglycemics (these are divided into prandial glucose regulators and alpha-glucosidase inhibitors) and PPAR modulating agents.

In another aspect of the invention, the compound of formula I, or a pharmaceutically acceptable salt, solvate, solvate of such a salt or a prodrug thereof, may be administered in association with a PPAR modulating agent. PPAR modulating agents include but are not limited to a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art.

In addition, the combination of the invention may be used in conjunction with a sulfonylurea. The present invention also includes a compound of the present invention in combination with a cholesterol-lowering agent. The cholesterol-lowering agents referred to in this application include but are not limited to inhibitors of HMG-CoA reductase (3-hydroxy-3-methylglutaryl coenzyme A reductase). Suitably the HMG-CoA reductase inhibitor is a statin.

In the present application, the term "cholesterol-lowering agent" also includes chemical modifications of the HMG-CoA reductase inhibitors, such as esters, prodrugs and metabolites, whether active or inactive.

The present invention also includes a compound of the present invention in combination with an inhibitor of the ileal bile acid transport system (IBAT inhibitor). The present invention also includes a compound of the present invention in combination with a bile acid binding resin.

According to an additional further aspect of the present invention there is provided a combination treatment comprising the administration of an effective amount of a compound of the formula I, or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from: a CETP (cholesteryl ester transfer protein) inhibitor; a cholesterol absorption antagonist; a MTP (microsomal transfer protein) inhibitor; a nicotinic acid derivative, including slow release and combination products; a phytosterol compound; probucol; an anti-obesity compound, for example orlistat (EP 129,748) and sibutramine (GB 2,184,122 and U.S. Pat. No. 4,929,629); an antihypertensive compound, for example an angiotensin converting enzyme (ACE) inhibitor, an angiotensin II receptor antagonist, an andrenergic blocker, an alpha andrenergic blocker, a beta andrenergic blocker, a mixed alpha/beta andrenergic blocker, an andrenergic stimulant, calcium channel blocker, an AT-1 receptor blocker, a saluretic, a diuretic or a vasodilator; a CB1 antagonist or inverse agonist, for example rimonabant; another melanin concentrating hormone receptor I (MCHr1) antagonist; a PDK inhibitor; or modulators of nuclear receptors for example LXR, FXR, RXR, and RORalpha; an SSRI; a serotonin antagonist; or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Therefore, in an additional feature of the invention, there is provided a method for the treatment of type II diabetes and its associated complications in a warm-blooded animal, such as man, in need of such treatment which comprises administering to said animal an effective amount of a compound of formula I, or a pharmaceutically acceptable salt, solvate, solvate of such a salt or a prodrug thereof in simultaneous, sequential or separate administration with an effective amount of a compound from one of the other classes of compounds described in this combination section, or a pharmaceutically acceptable salt, solvate, solvate of such a salt or a prodrug thereof.

Therefore, in an additional feature of the invention, there is provided a method of treating hyperlipidemic conditions in a warm-blooded animal, such as man, in need of such treatment which comprises administering to said animal an effective amount of a compound of formula I, or a pharmaceutically acceptable salt, solvate, solvate of such a salt or a prodrug thereof in simultaneous, sequential or separate administration with an effective amount of a compound from one of the other classes of compounds described in this combination section or a pharmaceutically acceptable salt, solvate, solvate of such a salt or a prodrug thereof.

According to a further aspect of the invention, there is provided a pharmaceutical composition which comprises a compound of formula I, or a pharmaceutically acceptable salt, solvate, solvate of such a salt or a prodrug thereof, and a compound from one of the other classes of compounds described in this combination section or a pharmaceutically acceptable salt, solvate, solvate of such a salt or a prodrug thereof, in association with a pharmaceutically acceptable diluent or carrier.

According to a further aspect of the present invention, there is provided a kit comprising a compound of formula I, or a pharmaceutically acceptable salt, solvate, solvate of such a salt or a prodrug thereof, and a compound from one of the other classes of compounds described in this combination section or a pharmaceutically acceptable salt, solvate, solvate of such a salt or a prodrug thereof.

According to a further aspect of the present invention there is provided a kit comprising:

a) a compound of formula I, or a pharmaceutically acceptable salt, solvate, solvate of such a salt or a prodrug thereof, in a first unit dosage form;

b) a compound from one of the other classes of compounds described in this combination section or a pharmaceutically acceptable salt, solvate, solvate of such a salt or a prodrug thereof, in a second unit dosage form; and c) container means for containing said first and second dosage forms.

According to a further aspect of the present invention there is provided a kit comprising:

a) a compound of formula I, or a pharmaceutically acceptable salt, solvate, solvate of such a salt or a prodrug thereof, together with a pharmaceutically acceptable diluent or carrier, in a first unit dosage form;

b) a compound from one of the other classes of compounds described in this combination section or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula I, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the treatment of metabolic syndrome or type 2 diabetes and its associated complications in a warm-blooded animal, such as man.

According to another feature of the invention there is provided the use of a compound of the formula I, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula I, or a pharmaceutically acceptable salt, solvate, solvate of such a salt or a prodrug thereof, optionally together with a pharmaceutically acceptable diluent or carrier, with the simultaneous, sequential or separate administration of an effective amount of one of the other compounds described in this combination section, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

EXPERIMENTAL SECTION

The invention will now be described in more detail with the following examples that are not to be construed as limiting the invention.

ABBREVIATIONS

Ac acetyl
BSA bovine serum albumin
Bu butyl
t-Boc tert-butyloxycarbonyl
CHO Chinese hamster ovary (cells)
DCM methylene chloride, $CH_2Cl_2$
DEAD diethyl azodicarboxylate
DIPEA di-isopropyl-ethyl amine
DMF N,N-dimethylformamide
DMPU N,N'-dimethylpropyleneurea
DMSO dimethylsulfoxide
DTT dithiothreitol
EDTA ethylenediamine tetraacetic acid
ESI electrospray ionization
Et ethyl
GDP guanosine 5'-diphosphate
GPCR G-protein coupled receptor
GTP guanosine triphosphate
hERG human ether-a-go-go related gene (potassium ion channel)
HEPES N-2-hydroxyethyl piperazine-N'-2-ethanesulfonic acid
HPLC high performance liquid chromatography
LC liquid chromatography
MS mass spectroscopy
TEA triethylamine
TFA trifluoroacetic acid
THF tetrahydrofurane
Tris trishydroxymethylaminomethane
TPP triphenyl phosphine
t tert
rt. room temperature
sat. saturated
br broad
bd broad doublet
bs broad singlet
d doublet
bd broad doublet
dd doublet of doublets
ddd double doublet of doublets
dt doublet of triplets
m multiplet
q quartet
singlet
t triplet General Experimental Procedures Flash column chromatography was performed using Isolute Flash Si prepacked columns. Mass spectra were recorded on a Waters Micromass ZQ single quadrupole equipped with a pneumatically assisted electrospray interface (LC-MS).

HPLC analyses were performed on a Gynkotek P580 HPG, gradient pump with a Gynkotek UVD 170S UV-V is detector. Column: Chromolith Performance RP-18e, 4.6×100 mm, Mobile phase A: $CH_3CN$, Mobile phase B: 0.1% TFA (aq), Flow: 3 ml/min, Injection volume: 20 µl, Detection: 254 and 275 nm.

Purifications were performed on a Waters Prep LC 2000 with UV-detection, equipped with a Kromasil 10 µm C8 250 mm×20 mm column (or Kromasil 10 µm C8 300 mm×50 mm column.

Continuous flow hydrogenation was performed using a H-Cube HC-2 from Thales Nanotechnology Inc. equipped with a 30×4 mm CatCart (prepacked catalyst cartridge) of the appropriate catalyst (e.g. Raney-Nickel).

$^1H$ NMR and $^{13}C$ NMR spectra were obtained at 298 K on Varian Mercury Plus and Varian Inova instruments.

Chemical shifts are given in ppm with the solvent residual peak as internal standard: $CDCl_3$ $\delta_H$ 7.26, $\delta_C$ 77.2; MeOH-$d_4$ $\delta_H$ 3.31, $\delta_C$ 49.0; DMSO-$d_6$ $\delta_H$ 2.50; $\delta_C$ 39.5 ppm.

Chemical names (IUPAC) were generated using the software ACD/Name, version 9.00

Names/reference numbers of starting materials (CAS no or supplier code no), either commercially available or prepared according to literature procedures:

1-Methyl-piperidin-4-ol, 106-52-5; (1R,3R,5S)-8-methyl-8-aza-bicyclo[3.2.1]octan-3-ol, 120-29-6; 3-fluoro benzonitrile, 403-54-3; 5-(4-chloro-phenyl)-3-(dimethylamino-ethyleneamino)-thiophene-2-carboxylic acid methyl ester, 91076-93-6; 4-(2-amino-ethyl)-N-diethyl-benzamide, 885270-66-6; 3-(4-methyl-piperazin-1-yl)-benzylamine, 672325-37-0; 3-(4-methyl-piperazin-1-ylmethyl)-benzylamine, 515162-19-3; 3-(2-morpholin-4-yl-ethoxy)-benzylamine, 857284-08-3; 3-hydroxy-benzonitrile, 873-62-1; 2-chloro-5-(trifluoromethyl)-pyridine, 52334-81-3; 3-[(methylsulfonyl)oxy]benzyl methanesulfonate, 82517-86-0; 2-[4-(trifluoromethyl)phenyl]thieno[2,3-d]pyridazin-7(6H)-one, 868662-16-2; 5-(4-chlorophenyl)thiophene-2-carboxylic acid, 40133-14-0; (3R)-pyrrolidin-3-ol, 2799-21-5; 6-bromo-2-pyridinecarbonitrile, 122918-25-6; 2-chloro-4 pyridinecarbonitrile, 33252-30-1; 1-methylpiperidin-3-ol, 3554-74-3; tert-butyl 4-hydroxypiperidine-1-carboxylate, 109384-19-2; (1-methylpiperidin-4-yl)methanol, 20691-89-8; (1,4-dimethylpiperazin-2-yl)methanol, 14675-44-6; (1-methylpyrrolidin-3-yl)methanol, CHEMBRIDGE-BB 4003799; (3R)-quinuclidin-3-ol, 25333-42-0; 1-isopropylpiperidin-4-ol, 5570-78-5; (1,3-dimethylpiperidin-3-yl)methanol, CHEMBRIDGE-BB 4016764; (6-bromopyridin-2-yl)methanol, 33674-96-3; tert-butyl 4-hydroxypiperidine-1-carboxylate, 109384-19-2; 2-(4-methoxyphenyl)thieno[2,3-d]pyridazin-7(6H)-one, 897662-01-0; tert-butyl (2S)-2-(hydroxymethyl)piperidine-1-carboxylate, 134441-93-3; [(2S)-1-methylpyrrolidin-2-yl]methanol, 34381-71-0; tert-butyl (2R)-2-(hydroxymethyl)pyrrolidine-1-carboxylate, 83435-58-9.

In order that the invention disclosed herein may be more efficiently understood, examples are provided below. It should be understood that these examples are for illustrative purposes only and are not to be construed as limiting the invention in any manner.

EXAMPLES

Example 1

6-(4-Chlorophenyl)-3-(3-{[(3-en do)-8-methyl-8-azabicyclo[3.2.1]oct-3-yl]oxy}benzyl)thieno[3,2-d]pyrimidin-4(3H)-one

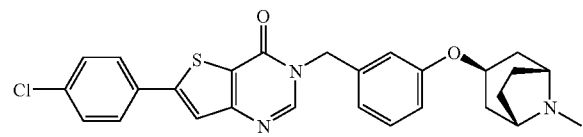

a) 3-{[(3-Endo)-8-methyl-8-azabicyclo[3.2.1]oct-3-yl]oxy}benzonitrile

To a solution of (1R,3R,5S)-8-methyl-8-aza-bicyclo[3.2.1]octan-3-ol (3.45 g, 24.4 mmol) in dry DMF (35 mL) at 0° C., 60% sodium hydride (1.76 g, 36.6 mmol) was added in portions over a period of 30 minutes. The reaction mixture was stirred at 0° C. for 30 minutes. 3-Fluoro benzonitrile (2.97 g, 24.5 mmol) in dry DMF (10 mL) was added dropwise over a period of 30 minutes. The reaction mixture was slowly brought to r.t. Due to excessive foaming the reaction mixture was diluted with dry DMF to 100 mL. The reaction mixture was then stirred at r.t. over night under argon. The reaction mixture was cooled to 0° C. and quenched with water. The product was extracted with EtOAc. The organic layer washed with brine, dried over MgSO$_4$ and concentrated in vacuo. The product was purified by flash chromatography using a gradient with toluene:EtOAc:MeOH:TEA (1:1:0.1:0.05) against toluene, which gave the product as a yellow oil. Yield: 4.10 g (69%). $^1$H NMR (400 MHz, CD$_3$OD) δ 7.41 (t, 1H, J=7.67 Hz), 7.23 (d, 1H, J=7.67 Hz), 7.12-7.19 (m, 2H), 4.59 (m, 1H), 3.13 (bs, 2H), 2.27 (s, 3H), 2.15 (t, 1H, J=4.32 Hz), 2.11 (t, 1H, J=4.32 Hz), 2.04 (s, 4H), 1.90 (s, 1H), 1.86 (s, 1H). MS (ESI+) 243 (M+1H$^+$).

b) 1-(3-{[(3-endo)-8-methyl-8-azabicyclo[3.2.1]oct-3-yl]oxy}phenyl)methanamine

A solution of 3-{[(3-Endo)-8-methyl-8-azabicyclo[3.2.1]oct-3-yl]oxy}benzonitrile (3.60 g, 14.8 mmol) in MeOH (50 mL) was purged with ammonia for 5 min, Raney Nickel was added and the mixture was placed under H$_2$ at 3 bar for 6 hours. The reaction mixture was filtered over celite and evaporated in vacuo. The crude product was purified by flash chromatography to give the title compound. Yield: 2.00 g (55%). MS (ESI+) 247.11 (M+1H$^+$).

c) 6-(4-chlorophenyl)-3-(3-{[(3-endo)-8-methyl-8-azabicyclo[3.2.1]oct-3-yl]oxy}benzyl)thieno[3,2-d]pyrimidin-4(3H)-one 5-(4-Chloro-phenyl)-3-(dimethylamino-methylene-amino)-thiophene-2-carboxylic acid methyl ester (1.25 g, 3.87 mmol), 1-(3-{[(3-endo)-8-methyl-8-azabicyclo[3.2.1]oct-3-yl]oxy}phenyl)methanamine (0.80 g, 3.25 mmol) and phenol (7.0 g) were stirred at 130° C. for 2 hours. The reaction mixture was allowed to cool to r.t. and the product precipitated by the addition of MeOH (20 mL). The off-white precipitate was filtered off and washed with MeOH (50 mL) to give the title compound. Yield: 0.138 g (60%). $^1$H NMR (400 MHz, CDCl$_3$) δ 8.08 (s, 1H), 7.61 (d, 2H, J=8.86 Hz), 7.45 (s, 1H), 7.41 (d, 2H, J=8.86 Hz), 7.23 (s, 1H), 6.86 (d, 1H, J=7.82 Hz), 6.81 (bs, 1H), 6.75 (dd, 1H, J=8.31 Hz, J=2.16 Hz), 5.16 (s, 2H), 4.48 (m, 1H), 3.07 (bs, 2H), 2.26 (s, 3H), 1.85-2.10 (m, 8H). MS (ESI+) 491.92 (M+1H$^+$).

Example 2

6-(4-Chlorophenyl)-3-{3-[(1-methylpiperidin-4-yl)oxy]benzyl}thieno[3,2-d]pyrimidin-4(3H)-one a) 3-(1-Methyl-piperidin-4-yloxy)-benzonitrile 1-Methyl-piperidin-4-ol (7.17 g, 62.25 mmol) was dissolved in DMF (40 ml) and cooled to 0° C. NaH (4.48 g, 93.4 mmol) was added in small portions and the reaction stirred for 30 min. 3-Fluoro-benzonitrile (8.0 ml, 74.7 mmol) was added and the reaction allowed to reach r.t. over 1 h and stirred for a further 16 h. The resulting brown solution was cooled to 0° C. and quenched by addition of water. The reaction mixture was separated between DCM (500×2 ml) and water (750 ml). The combined organics were washed with water (500 ml), dried through a phase separator and evaporated in vacuo. Flash silica gel chromatography using a 100 g Biotage column with a gradient of 20-100% EtOAc/MeOH/TEA 100:10:1 in heptane failed to give a pure product. The oil was dissolved in 0.1 M KHSO4 (aq) and washed with ether (×4), the aqueous layer basified (2 M NaOH (aq)) and extracted twice with ether. The organic phase was dried over a phase separator and evaporated in vacuo. To the red brown oil was added 4M HCl in dioxane and the resulting precipitate was filtered. To the salt was added 10% NaHCO3 (aq), extracted with DCM, dried through a phase separator and evaporated in vacuo to give a light orange oil. Yield: 4.73 g (29%). $^1$H NMR (400 MHz, CDCl$_3$) δ 7.35 (t, 1H, J$_{HH}$=7.84 Hz), 7.21 (dt, 1H, J=7.39 Hz, J=1.06 Hz), 7.15-7.10 (m, 2H), 4.32 (m, 1H, J=3.74 Hz), 2.68 (m, 2H), 2.33-2.24 (m, 5H), 2.04-1.95 (m, 2H), 1.88-1.78 (m, 2H). MS (ESI+) 217.07 (M+1H$^+$).

b) 3-(1-Methyl-piperidin-4-yloxy)-benzylamine 3-(1-Methyl-piperidin-4-yloxy)-benzonitrile (1.20 g, 5.55 mmol) was dissolved (0.05 M) in NH$_3$ in MeOH (111 ml).

Hydrogenation was performed using a Raney-Ni 30×4 mm CatCart (H-Cube, 50 bar, 50° C., 1 ml/min). Evaporation in vacuo yielded a light orange oil. Yield: 1.16 g (95%). $^1$H NMR (400 MHz, CDCl$_3$) δ 7.25-7.17 (m, 1H), 8-6.83 (m, 2H), 6.78-6.73 (dd, J=7.67 Hz, J=2.05 Hz), 4.32 (m, 1H), 3.80 (s, 2H), δ 2.69 (m, 2H), 2.36-2.25 (m, 5H), 2.05-1.95 (m, 2H), 1.88-1.72 (m, 4H). MS (ESI+) 221.1 (M+1H$^+$).

c) 6-(4-chlorophenyl)-3-{3-[(1-methylpiperidin-4-yl)oxy]benzyl}thieno[3,2-d]pyrimidin-4(3H)-one 5-(4-Chloro-phenyl)-3-(dimethylamino-methylene-amino)-thiophene-2-carboxylic acid methyl ester (0.100 g, 0.310 mmol), 3-(1-methyl-piperidin-4-yloxy)-benzylamine (0.109 g, 0.370 mmol) and phenol (1.0 g) were stirred at 130° C. for 2 hours. The reaction mixture was allowed to cool to r.t. and the product was partially purified by flash chromatography using a gradient elution with n-heptane against MeOH/TEA. The fractions containing the title product were concentrated in vacuo and purified further by washing with MeOH to give the title compound. Yield: 0.052 g (36%). $^1$H NMR (400 MHz, CDCl$_3$) δ 8.08 (s, 1H), 7.61 (d, 2H, J=8.52 Hz), 7.45 (s, 1H), 7.41 (d, 2H, J=8.52 Hz), 7.24 (m, 1H), 6.89 (m, 2H), 6.83 (d, 1H, J=9.02 Hz), 5.16 (s, 2H), 4.29 (bs, 1H), 2.65 (bs, 2H), 2.21-2.31 (m, 5H), 1.95 (m, 2H), 1.79 (m, 2H). MS (ESI+) 465.93 (M+1H$^+$).

Example 3

4-{2-[6-(4-Chlorophenyl)-4-oxothieno[3,2-d]pyrimidin-3(4H)-yl]ethyl}-N,N-diethylbenzamide 5-(4-Chloro-phenyl)-3-(dimethylamino-methylene-amino)-thiophene-2-carboxylic acid methyl ester (0.100 g, 0.310 mmol), 4-(2-amino-ethyl)-N,N-diethyl-benzamide (0.082 g, 0.372 mmol) and phenol (1.0 g) were stirred at 135° C. for 2 hours. The reaction mixture was allowed to cool to r.t. and the product precipitated by the addition of MeOH (16 mL). The precipitate was filtered off and washed with MeOH to give the title compound. Yield: 0.058 g (40%). $^1$H NMR (400 MHz, CDCl$_3$) δ 7.69 (s, 1H), 7.61 (d, 2H, J=8.67 Hz), 7.39-7.44 (m, 3H), 7.30 (d, 2H, J=8.19 Hz), 7.18 (d, 2H, J=8.19 Hz), 4.23 (t, 2H, J=7.05 Hz), 3.51 (bs, 1H), 3.46 (d, 2H, J=5.39 Hz), 3.21 (bs, 1H), 3.12 (t, 2H, J=6.64 Hz), 1.21 (bs, 3H), 1.08 (bs, 3H).

Example 4

6-(4-Chlorophenyl)-3-[3-(4-methylpiperazin-1-yl)benzyl]thieno[3,2-d]pyrimidin-4(3H)-one A mixture of 5-(4-chloro-phenyl)-3-(dimethylamino-methyleneamino)-thiophene-2-carboxylic acid methyl ester (0.189 g, 0.585 mmol), 3-(4-methyl-piperazin-1-yl)-benzylamine (0.100 g, 0.487 mmol) and phenol (1.0 g) was stirred at 130° C. for 1.5 hours. The reaction mixture was allowed to cool to r.t. and MeOH (10 mL) was added. After 30 minutes the precipitate was filtered off and washed with MeOH (50 mL). The crude product was purified by flash chromathography using a mixture of EtOAc, MeOH and TEA as eluent to give the product as an off white solid. Yield: 0.079 g (30%). $^1$H NMR (400 MHz, CDCl$_3$) δ 8.08 (s, 1H), 7.60 (d, 2H, J=7.92 Hz), 7.44 (s, 1H), 7.40 (d, 2H, J=7.92 Hz), 7.22 (m, 1H), 6.92 (bs, 1H), 6.85 (d, 1H, J=7.92 Hz), 6.79 (d, 1H, J=7.46 Hz), 5.15 (s, 2H), 3.19 (m, 4H), 2.53 (m, 4H), 2.32 (s, 3H). MS (ESI+) 450.95 (M+1H$^+$).

Example 5

6-(4-Chlorophenyl)-3-{3-[(4-methylpiperazin-1-yl)methyl]benzyl}thieno[3,2-d]pyrimidin-4(3H)-one 5-(4-Chloro-phenyl)-3-(dimethylamino-methylene-amino)-thiophene-2-carboxylic acid methyl ester (0.177 g, 0.547 mmol), 3-(4-methyl-piperazin-1-ylmethyl)-benzylamine (0.100 g, 0.456 mmol) and phenol (1.00 g) were stirred at 130° C. for 1.5 hours. The reaction mixture was allowed to cool to r.t. The product was partly purified by flash chromatography using EtOAc, MeOH and TEA mixtures as eluent to give a yellow solid. The solid was washed with MeOH to give the product. Yield: 0.122 g (48%). $^1$H NMR (400 MHz, CDCl$_3$) δ 8.11 (s, 1H), 7.63 (d, 2H, J=8.52 Hz), 7.45 (s, 1H), 7.43 (d, 2H, J=8.52 Hz), 7.21-7.34 (m, 4H), 5.20 (s, 2H), 3.47 (s, 2H), 2.41 (bs, 8H), 2.25 (s, 3H). MS (ESI+) 464.93 (M+1H$^+$).

Example 6

6-(4-Chlorophenyl)-3-[3-(2-morpholin-4-yl-ethoxy)benzyl]thieno[3,2-d]pyrimidin-4(3H)-one 5-(4-Chlorophenyl)-3-(dimethylamino-methylene-amino)-thiophene-2-carboxylic acid methyl ester (0.164 g, 0.508 mmol), 3-(2-morpholin-4-yl-ethoxy)-benzylamine (0.100 g, 0.423 mmol) and MeOH (1.5 mL) were heated by MW at 120° C. for 15 minutes. The reaction mixture was allowed to cool to r.t., the precipitate filtered, washed with MeOH, and dried in vacuo to give the product. Yield: 0.110 g (45%). $^1$H NMR (400 MHz, CDCl$_3$) δ 8.11 (s, 1H), 7.63 (d, 2H, J=8.42 Hz), 7.45 (s, 1H), 7.41 (d, 2H, J=8.42 Hz), 7.25 (m, 1H), 6.81-6.94 (m, 3H), 5.17 (s, 2H), 4.06 (t, 2H, J=6.12 Hz), 3.70 (t, 4H, J=4.68 Hz), 2.75 (t, 2H, J=5.58 Hz), 2.53 (t, 4H, J=4.51 Hz). MS (ESI+) 481.92 (M+1H$^+$).

Example 7

6-(4-Chlorophenyl)-3-(3-{[(3-exo)-8-methyl-8-azabicyclo[3.2.1]oct-3-yl]oxy}benzyl)-3H-thieno-[3,2-d]pyrimidin-4-one, acetate salt

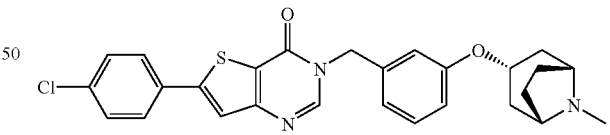

a) 3-{[(3-Exo)-8-methyl-8-azabicyclo[3.2.1]oct-3-yl]oxy}benzonitrile, hydrochloride salt 3-Hydroxy-benzonitrile (1.0 g, 8.5 mmol), (1R,3R,5S)-8-Methyl-8-aza-bicyclo[3.2.1]octan-3-ol (1.4 g, 10.2 mmol), and TPP (2.2 g, 8.5 mmol) was dissolved in THF (30 mL) and cooled to 0° C. DEAD (3.9 mL, 8.5 mmol, 40% in toluene) was added dropwise to the reaction mixture at 0° C. The reaction mixture was allowed to reach ambient temperature and was stirred for 72 h. The solvent was evaporated and the residue was dissolved in ether followed by addition of 4M HCl in dioxane (3 mL) and the precipitate was isolated. The precipitate was dissolved in methanol/water and the methanol was evaporated the isolated precipitate washed several times with water to give the title compound as its HCl salt. Yield: 0.7 g (34%). $^1$H NMR (300 MHz, CD$_3$OD) δ 7.51-7.43 (m, 1H), 7.40-7.36 (m, 1H), 7.36-7.28 (m, 2H), 4.99-4.87 (m, 1H), 4.05-3.96 (m, 2H), 2.84 (s, 3H), 2.5-2.18 (m, 6H), 2.13-1.94 (m, 2H). MS (ESI+) 243.1 (M+1H$^+$)

b) 1-(3-{[(3-Exo)-8-methyl-8-azabicyclo[3.2.1]oct-3-yl]oxy}phenyl)methanamine

3-{[(3-Exo)-8-methyl-8-azabicyclo[3.2.1]oct-3-yl]oxy}benzonitrile×HCl (0.6 g, 2.15 mmol) was dissolved in ether/2M NaOH and extracted with ether. The organic solvent was evaporated and the residue was dissolved in NH$_3$ (MeOH) (40 mL) and was hydrogenated at 50 bar, 50° C., and 1 ml/min through a R$^a$—Ni flow cell. The solvent was evaporated to give the title compound. Yield: 532 mg (99%). $^1$H NMR (300 MHz, CD$_3$OD) δ 7.20 (t, 1H, J=7.8 Hz), 6.93-6.83 (m, 2H), 6.81-6.76 (m, 1H), 4.67-4.53 (m, 1H), 3.74 (s, 2H), 3.29-3.22 (m, 2H), 2.32 (s, 3H), 2.16-1.98 (m, 4H), 1.85-1.69 (m, 4H). $^{13}$C NMR (100 MHz, CD$_3$OD) δ 159.34, 145.15, 130.59, 121.00, 116.07, 115.68, 70.45, 61.84, 46.61, 39.16, 37.45, 27.17. MS (ESI+) 247 (M+1H$^+$).

c) 6-(4-Chlorophenyl)-3-(3-{[(3-exo)-8-methyl-8-azabicyclo[3.2.1]oct-3-yl]oxy}benzyl)thieno[3,2-d]pyrimidin-4(3H)-one, acetate salt 1-(3-{[(3-Exo)-8-methyl-8-azabicyclo[3.2.1]oct-3-yl]oxy}phenyl)methanamine (263 mg, 1.07 mmol) and methyl 5-(4-chlorophenyl)-3-{[(1E)-(dimethylamino)methylene]amino}thiophene-2-carboxylate (345 mg, 1.07 mmol) were dissolved in methanol (3 mL) and the solution was heated to 120° C. in a microwave reactor for 10 min. Water was added and the precipitate was rinsed with methanol/water (10:90). The precipitate was purified with preparative HPLC using a 0.2% AcOH/water/ACN gradient to yield the title compound. Yield: 238 mg (45%). $^1$H NMR (300 MHz, CDCl$_3$) δ 8.11 (s, 1H), 7.66-7.59 (m, 2H), 7.50-7.40 (m, 3H), 7.25 (t, J=8.1 Hz, 1H), 6.97-6.89 (m, 2H), 6.87-6.79 (m, 1H), 5.18 (s, 2H), 4.60-4.46 (m, 1H), 3.49 (s, 2H), 2.55 (s, 3H), 2.23 (s, 3H), 2.16-1.97 (m, 5H), 1.86-1.76 (m, 3H). $^{13}$C NMR (100.579 MHz, CDCl$_3$) δ 176.62, 158.28, 157.74, 157.16, 151.62, 148.20, 137.46, 135.86, 131.77, 130.37, 129.66, 127.88, 123.30, 121.04, 120.62, 116.20, 115.74, 69.63, 60.33, 49.50, 37.67, 35.10, 26.82, 22.88. ESI-MS calcd for C$_{27}$H$_{26}$ClN$_3$O$_2$S 492.1512 (M+1H$^+$). found 492.1478 (M+1H$^+$).

Example 8

2-(4-Chlorophenyl)-6-{3-[(1-methylpiperidin-4-yl)oxy]benzyl}thieno[2,3-d]pyridazin-7(6H)-one, acetate salt a) 5-(4-Chlorophenyl)-3-formylthiophene-2-carboxylic acid To a stirred solution 5-(4-chlorophenyl)thiophene-2-carboxylic acid (11 g, 0.046 mol) in dry THF (150 ml) was added n-BuLi (63 ml, 0.102 mol, 1.6 M solution in hexane) in a dropwise manner at −78° C. under inert atmosphere. The temperature was slowly raised to 0° C. over a period of 4 h. The reaction mixture was again cooled to −70° C. and dry DMF (34 ml, 0.43 mol) was added slowly. After completion of the addition of DMF, temperature was raised to −10° C. and stirred for 2 h. The reaction mixture was again cooled to −30° C. and 1.5 N HCl (50 ml) was added slowly and reaction was allowed to come to RT. The reaction mixture was extracted with EtOAc (4×200 ml). The combined organic layer washed with water (2×150 ml), brine (2×150 ml), dried (Na$_2$SO$_4$) and concentrated. The crude product washed with p-ether (100 ml) to afford 8 g of the title compound (65%). R$_f$=0.2 (CHCl$_3$:MeOH, 8:2). This was found pure enough to carry further. Since this intermediate is unstable it has to be used immediately in the next step.

b) 2-(4-Chlorophenyl)thieno[2,3-d]pyridazin-7(6H)-one

To a stirred solution of 5-(4-chlorophenyl)-3-formylthiophene-2-carboxylic acid (3 g, 0.011 mol) in ethanol (30 ml) was added hydrazine hydrate (0.65 ml, 0.013 mol) in small drops. To this was added conc. HCl (1.8 ml, 0.058 mol) in a dropwise manner and heated to 82° C. for 2 days. The reaction mixture was allowed to cool down and 10% NaHCO$_3$ (5 ml) was added slowly until pH=8. The solid was filtered, washed with water (200 ml) and dried to afford 2.1 g (71%) of the title compound. R$_f$=0.5 (CHCl$_3$:MeOH, 8:2). $^1$H NMR (400 MHz, DMSO-d$_6$) δ 12.98 (bs, 1H), 8.39 (s, 1H), 7.98 (s, 1H), 7.88 (d, 2H, J=8.6 Hz), 7.59 (d, 2H, J=8.6 Hz).

c) 2-(4-Chlorophenyl)-6-(3-hydroxybenzyl)thieno[2,3-d]pyridazin-7(6H)-one

To a stirred slurry of 2-(4-chlorophenyl)thieno[2,3-d]pyridazin-7(6H)-one (0.192 g, 0.73 mmol) in DMF (5 mL), under an atm of N$_2$, was added NaH (60%, 0.040 g, 1.0 mmol) and the resulting mixture stirred for 5 min. 3-[(Methylsulfonyl)oxy]benzyl methanesulfonate (0.246 g, 0.88 mmol) was added, and the resulting mixture stirred for 2 hours at room temperature. H$_2$O was added and the mixture concentrated. Residual DMF was removed by evaporation from toluene. MeOH (20 mL) and KOH (1.0 g, 18 mmol) were added and the resulting mixture was stirred over night. The mixture was neutralised with HOAc, concentrated and purified on C8-HPLC (0.1% HOAc, gradient 5→100% CH$_3$CN) to give 0.175 g (65%) of the title compound. $^1$H NMR (400 MHz, DMSO-d$_6$) δ 9.38 (s, 1H), 8.47 (s, 1H), 7.98 (s, 1H), 7.88 (d, 2H, J=8.5 Hz), 7.59 (d, 2H, J=8.5 Hz), 7.12 (dd, 1H, J=8.0, 7.7 Hz), 6.74 (d, 1H, J=7.7 Hz), 6.70 (s, 1H), 6.66 (d, 1H, J=8.0 Hz). MS (ESI+) 369 (M+1H$^+$), MS (ESI−) 367(M−1H$^+$).

d) 2-(4-Chlorophenyl)-6-{3-[(1-methylpiperidin-4-yl)oxy]benzyl}thieno[2,3-d]pyridazin-7(6H)-one, acetate salt 2-(4-Chlorophenyl)-6-(3-hydroxybenzyl)thieno[2,3-d]pyridazin-7(6H)-one (0.082 g, 0.22 mmol), 1-methylpiperidin-4-ol (0.050 g, 0.43 mmol) and TPP (0.107 g, 0.41 mmol) were stirred in THF (3 mL) at 0° C. DEAD (0.2 mL, 40% in toluene, 0.44 mmol) was added and the resulting mixture was allowed to attain room temperature and the stirring was continued over night. Concentration and purification on C8-HPLC (0.1% HOAc, gradient 30→40% CH$_3$CN) gave 0.019 g (16%) of the title compound. $^1$H NMR (400 MHz, CDCl$_3$/MeOH-d$_4$ 1:1, internal standard: MeOH-d$_4$) δ 8.30 (s, 1H), 7.66 (d, 2H, J=8.5 Hz), 7.59 (s, 1H), 7.43 (d, 2H, J=8.5 Hz), 7.22 (t, 1H, J=7.9 Hz), 7.03 (m, 2H), 6.83 (d, 1H, J=7.7 Hz), 5.39 (s, 2H), 4.53 (br, 1H), 3.07-2.86 (m, 4H), 2.59 (s, 3H), 2.16-1.94 (m, 4H), 1.97 (s, 3H). $^{13}$C NMR (100 MHz, CDCl$_3$/MeOH-d$_4$ 1:1, internal standard: MeOH-d$_4$) δ 177.1, 157.9, 157.5, 153.2, 141.2, 138.8, 136.5, 136.3, 134.7, 131.6, 130.4, 130.1, 128.6, 122.1, 119.9, 116.8, 115.8, 69.1, 51.1, 44.4, 28.8, 22.3. MS (ESI+) 466.1 (M+1H$^+$).

Example 9

6-{3-[(1-Methylpiperidin-4-yl)oxy]benzyl}-2-[4-(trifluoromethyl)phenyl]thieno[2,3-d]pyridazin-7(6H)-one, acetate salt a) 6-(3-Hydroxybenzyl)-2-[4-(trifluoromethyl)phenyl]thieno[2,3-d]pyridazin-7(6H)-one To a stirred slurry of 2-[4-(trifluoromethyl)phenyl]thieno[2,3-d]pyridazin-7(6H)-one
(0.500 g, 1.69 mmol) in DMF (5 mL), under an atm of N$_2$, was added NaH (60%, 0.100 g, 2.5 mmol) and the resulting mixture was stirred for 5 min. 3-[(Methylsulfonyl)oxy]benzyl methanesulfonate (0.473 g, 1.69 mmol) and DMF (5 mL) were added and the resulting mixture stirred for 2 hours at room temperature. 1M NaOH (2 mL) was added and the mixture stirred over night. An additional 0.5 g of NaOH was added and the mixture heated to 80° C. over night. An additional 0.5 g of NaOH and 5 ml H$_2$O were added and the mixture stirred for 30 min. The mixture was neutralized with HOAc, concentrated and purified on C8-HPLC (0.1% HOAc, gradient 5→100% CH$_3$CN) to give 0.355 g (52%) of the title compound. $^1$H NMR (400 MHz, DMSO-d$_6$) δ 9.39 (s, 1H), 8.51 (s, 1H), 8.11 (s, 1H), 8.08 (d, 2H, J=8.2 Hz), 7.89 (d, 2H, J=8.2 Hz), 7.12 (dd, 1H, J=8.1, 7.7 Hz), 6.75 (d, 1H, J=7.7 Hz), 6.71 (s, 1H), 6.66 (d, 1H, J=8.1 Hz).

b) 6-{3-[(1-Methylpiperidin-4-yl)oxy]benzyl}-2-[4-(trifluoromethyl)phenyl]thieno[2,3-d]pyridazin-7(6H)-one, acetate salt 6-(3-Hydroxybenzyl)-2-[4-(trifluoromethyl)phenyl]thieno[2,3-d]pyridazin-7(6H)-one (0.203 g, 0.50 mmol), 1-methylpiperidin-4-ol (0.074 g, 0.64 mmol) and TPP (0.172 g, 0.66 mmol) were stirred in THF (3 mL) at 0° C. DEAD (0.3 mL, 40% in toluene, 0.66 mmol) was added and the resulting mixture was allowed to attain room temperature and the stirring continued over night. Concentration and purification on C8-HPLC (0.1% HOAc, gradient 30→40% CH$_3$CN) gave 0.022 g (8%) of the title compound. $^1$H NMR (400 MHz, CDCl$_3$) δ 8.19 (s, 1H), 7.77 (d, 2H, J=8.3 Hz), 7.70 (d, 2H, J=8.3 Hz), 7.51 (s, 1H), 7.22 (dd, 1H, J=8.2, 7.7 Hz), 7.04 (d, 1H, J=7.7 Hz), 7.00 (bs, 1H), 6.78 (dd, 1H, J=8.2, 0.9 Hz), 5.37 (s, 2H), 4.44 (br, 1H), 2.88-2.72 (m, 4H), 2.45 (s, 3H), 2.15-2.05 (m, 2H), 1.99 (s, 3H), 1.98-1.88 (m, 2H). MS (ESI+) 500 (M+1H$^+$).

Example 10

6-(4-Chlorophenyl)-3-{3-[(3R)-3-hydroxypyrrolidin-1-yl]benzyl}thieno[3,2-d]pyrimidin-4(3H)-one a) 3-[(3R)-3-Hydroxypyrrolidin-1-yl]benzonitrile 3-Fluorobenzonitrile (0.385 g, 3.18 mmol) and (3R)-pyrrolidin-3-ol (0.278 g, 3.19 mmol) were dissolved in DMPU (3 mL). The resulting mixture was subjected to microwave heating at 180° C. for 5 h. Water was added and the mixture extracted with ether. The organic layer washed with water, dried with MgSO$_4$, filtered and concentrated. Purification on a 10 g Isolute Flash Si column (heptane/EtOAc 2:1→1:1) gave 0.375 g (63%) of the title compound. $^1$H NMR (400 MHz, MeOH-d$_4$) δ 7.22 (dd, 1H, J=8.5, 7.5 Hz), 6.82 (d, 1H, J=7.5 Hz), 6.72 (dd, 1H, J=8.5, 2.2 Hz), 6.69 (bs, 1H), 4.48 (m, 1H), 3.42-3.33 (m, 2H), 3.24 (ddd, 1H, J=8.8, 8.8, 3.4 Hz), 3.13 (bd, 1H, J=10.5 Hz), 2.14-1.94 (m, 2H). $^{13}$C NMR (MeOH-d$_4$) δ 149.2, 130.9, 120.6, 119.5, 117.0, 114.9, 113.4, 71.4, 56.7, 46.5, 34.7.

b) (3R)-1-[3-(Aminomethyl)phenyl]pyrrolidin-3-ol

To 3-[(3R)-3-hydroxypyrrolidin-1-yl]benzonitrile (0.070 g, 0.37 mmol) and 5% rhodium on alumina (15 mg) in abs EtOH (5 mL) was added NH$_4$OH (26%, 1 mL). The resulting mixture was stirred under H$_2$ over night. A second portion of 5% rhodium on alumina (30 mg) was added and the stirring under H$_2$ continued for 2 days. The mixture was filtered through Celite and concentrated to give 0.62 g (69%) of the title compound (purity ~80%). $^1$H NMR (400 MHz, CD$_3$OD) δ 7.10 (dd, 1H, J=8.1, 7.6 Hz), 6.56 (d, 1H, J=7.6 Hz), 6.51 (s, 1H), 6.42 (dd, 1H, J=8.1, 2.0 Hz), 4.47 (m, 1H), 3.69 (s, 1H), 3.47-3.36 (m, 2H), 3.32-3.24 (m, 1H), 3.17 (bd, 1H, J=9-7 Hz), 2.15-1.93 (m, 2H). $^{13}$C NMR (MeOH-d$_4$) δ 149.7, 143.4, 130.3, 115.8, 111.8, 111.7, 71.7, 57.0, 46.9, 46.7, 34.9.

c) 6-(4-Chlorophenyl)-3-{3-[(3R)-3-hydroxypyrrolidin-1-yl]benzyl}thieno[3,2-d]pyrimidin-4(3H)-one Methyl 5-(4-chlorophenyl)-3-{[(1E)-(dimethylamino)methylene]amino}thiophene-2-carboxylate (0.131 g, 0.41 mmol) and (3R)-1-[3-(aminomethyl)phenyl]pyrrolidin-3-ol (0.062 g, 0.26 mmol, purity 80%) in phenol (0.5 g) were subjected to microwave heating at 150° C. for 1 h. The product was precipitated with ether and decanted. The solid residue was washed with MeOH and CH$_2$Cl$_2$ to give 0.66 g (57%) of the title compound. $^1$H NMR (400 MHz, DMSO-d$_6$) δ 8.62 (s, 1H), 7.90 (s, 1H), 7.88 (d, 2H, J=8.7 Hz), 7.56 (d, 2H, J=8.7 Hz), 7.11 (t, 1H, J=7.9 Hz), 6.56-6.52 (m, 2H), 6.43 (d, 1H, J=7.5 Hz), 5.15 (s, 2H), 4.92 (d, 1H, J=7.5 Hz), 3.40-3.18 (m, 3H), 3.03 (bd, 1H, J=9-7 Hz), 2.07-1.95 (m, 1H), 1.91-1.82 (m, 1H). $^{13}$C NMR (100 MHz, DMSO-d$_6$) δ 157.6, 156.1, 149.8, 149.6, 147.8, 137.4, 134.3, 131.3, 129.4, 127.9, 121.8, 121.7, 114.1, 110.9, 110.7, 69.2, 55.9, 48.9, 45.4, 33.6. MS (ESI+) 438.1 (M+1H$^+$).

Example 11

6-(4-Chlorophenyl)-3-({6-[(1-methylpiperidin-4-yl)oxy]pyridin-2-yl}methyl)thieno[3,2-d]pyrimidin-4(3H)-one a) 6-[(1-Methylpiperidin-4-yl)oxy]pyridine-2-carbonitrile 1-Methylpiperidin-4-ol (1.89 g, 0.0164 mol), 6-bromo-2-pyridinecarbonitrile (3.00 g, 0.0164 mol), Pd(OAc)$_2$ (0.184 g, 0.820 mmol), 2-(di-t-butylphosphino)biphenyl (0.303 g, 1.02 mmol) and Cs(CO$_3$)$_2$ were mixed in 100 mL of toluene. The reaction mixture was stirred under argon and heated to 130° C. in an oil bath for 4 days. The reaction mixture was diluted with EtOAc and washed with water, dried over Na$_2$SO$_4$ and evaporated. The crude product was flash chromatographed on silica gel DCM/MeOH/TEA 95/5/1 to give 1.62 g (45%) of the desired product. $^1$H NMR (500 MHz, CDCl$_3$) δ 7.67 (m, 1H), 7.29 (d, 1H), 6.95 (d, 1H), 5.12 (m, 1H), 2.74 (m, 2H), 2.40-2.30 (m, 5H, thereof a singlet at 2.35), 2.09 (m, 2H), 1.86 (m, 2H).

b) 1-{6-[(1-Methylpiperidin-4-yl)oxy]pyridin-2-yl}methanamine

6-[(1-Methylpiperidin-4-yl)oxy]pyridine-2-carbonitrile (1.62 g, 7.46 mmol, from step a above) was dissolved in 150 mL of ammonia saturated MeOH and hydrogenation was performed using a Raney-Ni 30×4 mm CatCart (H-Cube, 50 bar, 50° C., 1 mL/min). The mixture was evaporated and was pure enough to use directly in the next step below. Yield: 1.62 g (98%). $^1$H NMR (500 MHz, CDCl$_3$) δ 7.50 (m, 1H), 6.75 (d, 1H), 6.56 (d, 1H), 5.11 (m, 1H), 3.82 (s, 2H), 2.74 (m, 2H), 2.43-2.30 (m, 5H, thereof a singlet at 2.34), 2.07 (m, 2H), 1.87 (m, 2H).

c) 6-(4-Chlorophenyl)-3-({6-[(1-methylpiperidin-4-yl)oxy]pyridin-2-yl}methyl)thieno[3,2-d]pyrimidin-4(3H)-one Methyl 5-(4-chlorophenyl)-3-{[(1E)-(dimethylamino)methylene]amino}thiophene-2-carboxylate (1.39 g, 4.29 mmol) and 1-{6-[(1-methylpiperidin-4-yl)oxy]pyridin-2-yl}methanamine (0.950 g, 4.29 mmol, from step b above) were mixed with 4 g of phenol and heated to 130° C. on an oil bath for 1 h. When the mixture had cooled down it was diluted with 150 mL of diethyl ether. The mixture became opaque and left overnight. Very little had precipitated but when evaporation of ether was commenced much precipitate was formed and filtered off. The material was recrystallized from ethanol, filtered, washed with ethanol and dried to give 0.675 g (32%) of the desired compound. Mp 202-203° C. $^1$H NMR (600 MHz, CD$_3$OD) δ 8.43 (s, 1H), 7.75 (m, 2H), 7.65 (s, 1H), 7.60 (t, 1H), 7.45 (m, 2H), 6.95 (d, 1H), 6.55 (d, 1H), 5.30 (s, 2H), 4.55 (br, 1H), 2.52 (m, 2H), 2.05 (s, 3H), 1.84 (m, 2H), 1.70 (m, 2H), 1.51 (m, 2H). $^{13}$C NMR (100 MHz, CDCl$_3$) δ 162.7, 157.9, 157.0, 151.9, 151.6, 149.1, 140.1, 135.9, 131.7, 129.7, 127.9, 123.0, 121.1, 115.7, 111.2, 51.4, 50.3, 44.6, 28.7, 22.1. MS (ESI+) 467/469 (M+1H$^+$).

Example 12

6-(4-Chlorophenyl)-3-{3-[(1-methylpiperidin-3-yl)oxy]benzyl}thieno[3,2-d]pyrimidin-4(3H)-one a) 3-[(1-Methylpiperidin-3-yl)oxy]benzonitrile

1-Methylpiperidin-3-ol (500 mg, 4.341 mmol) was dissolved in DMF (10 ml) and cooled to 0° C. NaH (312 mg, 6.52 mmol) was added in small portions, stirred for 30 minutes and 3-fluorobenzonitrile (557 μl, 5.21 mmol) was subsequently added. The mixture was allowed to reach r.t. over 1 h and stirred for a further 16 h. Cooled to 0° C. and quenched with water. The reaction mixture was separated between water (150 ml) and DCM (2×150 ml). The combined organics were washed with water (150 ml), dried through a phase separator and evaporated in vacuo. Purification by flash silica gel chromatography using a 40 g Biotage column with a gradient of 10-100% EtOAc/MeOH/TEA 100:10:1 in heptane yielded the title compound as a colorless oil. Yield: 0.628 g (56%). $^1$H NMR (400 MHz, CDCl$_3$) δ 7.32 (dt, 1H, J=7.6 Hz, J=0.9 Hz), 7.19 (m, 1H), 7.16-7.11 (m, 2H), 4.36 (m, 1H, J=4.0 Hz), 2.84 (m, 1H), 2.55 (m, 1H), 2.30-2.11 (m, 5H), 1.94 (m, 1H), 1.82 (m, 1H), 1.67-1.43 (m, 2H).

b) 1-{3-[(1-Methylpiperidin-3-yl)oxy]phenyl}methanamine

3-[(1-Methylpiperidin-3-yl)oxy]benzonitrile (623 mg, 2.90 mmol) was dissolved (0.05 M) in NH$_3$ in MeOH (58 ml). Hydrogenation was performed using a Raney-Ni 30×4 mm CatCart (H-Cube, 50 bar, 50° C., 1 ml/min). Evaporation in vacuo yielded the title compound as a colorless oil. Yield: 633 mg (99%). $^1$H NMR (400 MHz, CDCl$_3$) δ 7.20 (t, 1H, J=7.9 Hz), 6.89-6.83 (m, 2H), 6.79 (dd, 1H, J=8.2 Hz, J=2.2 Hz), 4.37 (m, 1H, J=4.2 Hz), 3.80 (s, 2H), 2.91 (d, 1H), 2.62-2.54 (m, 1H), 2.28 (s, 3H), 2.13 (m, 2H), 1.97 (m, 1H), 1.86-1.76 (m, 1H), 1.69-1.54 (m, 3H), 1.52-1.40 (m, 1H).

c) 6-(4-Chlorophenyl)-3-{3-[(1-methylpiperidin-3-yl)oxy]benzyl}thieno[3,2-d]pyrimidin-4(3H)-one Methyl 5-(4-chlorophenyl)-3-{[(1E)-(dimethylamino)methylene]amino}thiophene-2-carboxylate (180 mg, 0.558 mmol) and 1-{3-[(1-methylpiperidin-3-yl)oxy]phenyl}methanamine (135 mg, 0.613 mmol) were dissolved in MeOH (2 ml). The reaction was heated in a microwave at 120° C. for 15 minutes, MeOH added, the resulting precipitate filtered and washed with MeOH to yield the title compound as a white solid. Yield: 140 mg (54%). $^1$H NMR (400 MHz, d$_6$-DMSO) δ 8.66 (s, 1H), 7.92-7.87 (m, 3H), 7.57 (m, 2H), 7.25 (t, 1H, J=8.0 Hz), 6.94 (m, 1H), 6.89 (m, 2H), 5.18 (s, 2H), 4.36 (m, 1H J=4.3 Hz), 3.30 (d, 1H, J=9.6 Hz), 2.81 (d, 1H, J=10.7 Hz), 2.15 (s, 3H), 2.04-1.88 (m, 3H), 1.73-1.67 (m, 1H), 1.57-1.45 (m, 1H), 1.36-1.25 (m, 1H). MS (ESI+) 465.93 (M+1H$^+$).

Example 13

6-(4-Chlorophenyl)-3-{3-[(1-methylpiperidin-4-yl)methoxy]benzyl}thieno[3,2-d]pyrimidin-4(3H)-one a) 3-[(1-Methylpiperidin-4-yl)methoxy]benzonitrile (1-Methylpiperidin-4-yl)methanol (0.500 g, 3.87 mmol) was dissolved in dry DMF (8 mL), cooled (<0° C.), NaH (0.232 g, 5.80 mmol, 55% in oil) added and stirred for 30 minutes. 3-fluorobenzonitrile (0.492 g, 4.06 mmol) was added and the reaction mixture allowed to warm to r.t. over 1 hour. Due to excessive foaming the reaction mixture was diluted with dry DMF to 20 mL and stirred over night at r.t. The reaction was quenched by addition of water portionwise, and the mixture was extracted with EtOAc. The organics were dried (MgSO$_4$) and concentrated in vacuo. The product was purified by flash chromatography using a step gradient of EtOAc:MeOH:TEA (100:10:2) in EtOAc to give the title compound as an oil. Yield: 0.417 g (44%). $^1$H NMR (400 MHz, CDCl$_3$) δ 7.29-7.35 (m, 1H), 7.19 (m, 1H), 7.05-7.10 (m, 2H), 3.78 (d, 2H, J=6.1 Hz), 2.83-2.90 (m, 2H), 2.26 (s, 3H), 1.89-1.98 (m, 2H), 1.70-1.84 (m, 3H), 1.33-1.46 (m, 2H).

b) 1-{3-[(1-Methylpiperidin-4-yl)methoxy]phenyl}methanamine

3-[(1-Methylpiperidin-4-yl)methoxy]benzonitrile (0.417 g, 1.81 mmol) was dissolved in MeOH/NH$_3$(sat) (0.05M) and hydrogenated over a Raney Nickel CatCart (30×4 mm) using the H-Cube system (50 bar, 50° C., 1 mL/min). The product was concentrated and dried in vacuo, to give the title compound as an oil. Yield: 0.371 g (87%). $^1$H NMR (400 MHz, CD$_3$OD) δ 7.18 (t, 1H, J=8.1 Hz), 6.83-6.89 (m, 2H), 6.75 (dd, 1H, J=8.1 Hz, J=2.1 Hz), 4.82 (s, 2H), 3.80 (d, 2H, J=6.1 Hz), 3.71 (s, 2H), 2.84-2.91 (m, 2H), 2.46 (s, 3H), 1.97-2.06 (m, 2H), 1.79-1.87 (m, 2H), 1.70-1.79 (m, 1H), 1.33-1.46 (m, 2H).

c) 6-(4-Chlorophenyl)-3-{3-[(1-methylpiperidin-4-yl)methoxy]benzyl}thieno[3,2-d]pyrimidin-4(3H)-one 5-(4-Chloro-phenyl)-3-(dimethylamino-methyleneamino)-thiophene-2-carboxylic acid methyl ester (0.165 g, 0.51 mmol) and 1-{3-[(1-methylpiperidin-4-yl)methoxy]phenyl}-methanamine (0.100 g, 0.43 mmol) in MeOH (2 mL) was heated by microwave at 120° C. in 20 minutes, cooled, the formed precipitate filtered off and washed with MeOH to give the title compound as a white solid. Yield: 0.075 g (31%). $^1$H NMR (400 MHz, CDCl$_3$) δ 8.07 (s, 1H), 7.58-7.63 (m, 2H), 7.45 (s, 1H), 7.38-7.43 (m, 2H), 7.22 (m, 1H), 6.79-6.91 (m, 3H), 5.17 (s, 2H), 3.76 (d, 2H, J=6.4 Hz), 2.82-2.89 (m, 2H), 2.25 (s, 3H), 1.87-1.96 (m, 2H), 1.76-1.83 (m, 2H), 1.68-1.76 (m, 1H), 1.32-1.44 (m, 2H).

Example 14

6-(4-Chlorophenyl)-3-[3-(piperidin-4-yloxy)benzyl]thieno[3,2-d]pyrimidin-4(3H)-one a) tert-Butyl 4-(3-cyanophenoxy)piperidine-1-carboxylate tert-Butyl 4-hydroxypiperidine-1-carboxylate (3.49 g, 17.3 mmol) was dissolved in DMF (35 ml) and cooled to 0° C. NaH (1.19 g, 24.8 mmol) was added in small portions over 20 minutes. The reaction was stirred for 30 minutes at 0° C. and 3-fluorobenzonitrile (3.1 ml, 29.0 mmol) added. The reaction was allowed to warm to r.t. over 1 h, stirred for a further 16 h and then quenched by addition of water. The reaction mixture was separated between water (500 ml) and DCM (2×500 ml). The combined organics were washed with water (500 ml), dried through a phase separator and evaporated in vacuo. Purification by flash silica gel chromatography using a 100 g Biotage column with a gradient of 5-40% EtOAc in heptane yielded the title compound as a white solid. Yield: 4.2 g (81%). $^1$H NMR (400 MHz, CDCl$_3$) δ 7.34 (t, 1H, J=7.9 Hz), 7.21 (d, 1H, J=7.7), 7.14-7.08 (m, 2H), 4.46 (m, 1H), 3.67 (m, 2H), 3.33 (m, 2H), 1.90 (m, 2H), 1.72 (m, 2H), 1.45 (s, 9H).

b) tert-Butyl 4-[3-(aminomethyl)phenoxy]piperidine-1-carboxylate

Prepared from tert-butyl 4-(3-cyanophenoxy)piperidine-1-carboxylate (3.89 g, 13.95 mmol) according to the procedure in example 13b. Evaporation in vacuo yielded the title compound as a colorless oil. Yield: 4.20 g (98%). $^1$H NMR (400 MHz, CDCl$_3$) δ 7.21 (m, 1H), 6.89-6.85 (m, 2H), 6.76 (m, 1H), 4.46 (m, 1H), 3.82 (s, 2H), 3.67 (m, 2H), 3.31 (m, 2H), 1.93-1.84 (m, 2H), 1.77-1.68 (m, 2H), 1.44 (s, 9H).

c) tert-Butyl 4-(3-{[6-(4-chlorophenyl)-4-oxothieno[3,2-d]pyrimidin-3(4H)-yl]methyl}phenoxy)piperidine-1-carboxylate Methyl 5-(4-chlorophenyl)-3-{[(1E)-(dimethylamino)methylene]amino}thiophene-2-carboxylate (522 mg, 1.62 mmol) and tert-butyl 4-[3-(aminomethyl)phenoxy]piperidine-1-carboxylate (544 mg, 1.78 mmol) were dissolved in MeOH (10 ml). The mixture was heated in a microwave for 30 minutes at 120° C. A precipitate was formed from MeOH. The precipitate was filtered off and washed with MeOH yielding the title compound as a white solid. Yield: 431 mg (48%). $^1$H NMR (400 MHz, CDCl$_3$) δ 8.11 (s, 1H), 7.63 (m, 2H), 7.47 (s, 1H), 7.43 (m, 2H), 7.30-7.25 (m, 1H), 6.95-6.91 (m, 2H), 6.86 (m, 1H), 5.19 (s, 2H), 4.46 (m, 1H), 3.67 (m, 2H), 3.33 (m, 2H), 1.94-1.85 (m, 2H), 1.77-1.67 (m, 2H), 1.54 (s, 9H).

d) 6-(4-Chlorophenyl)-3-[3-(piperidin-4-yloxy)benzyl]thieno[3,2-d]pyrimidin-4(3H)-one tert-Butyl 4-(3-{[6-(4-chlorophenyl)-4-oxothieno[3,2-d]pyrimidin-3 (4 h-7)-yl]methyl}phenoxy)-piperidine-1-carboxylate was stirred in a mixture of 4 M HCl in Dioxane (5 ml) and MeOH (2 ml) for 2 h. The solvents were evaporated in vacuo. The resulting solid was taken up in DCM and washed with 10% NaHCO$_3$ (aq), dried through a phase separator and evaporated in vacuo yielding the title compound as a white solid. Yield: 290 mg (82%). $^1$H NMR (400 MHz, CDCl$_3$) δ 8.11 (s, 1H), 7.63 (m, 2H), 7.47 (s, 1H), 7.43 (m, 2H), 7.29-7.24 (m, 1H), 6.93-6.90 (m, 2H), 6.88-6.84 (m, 1H), 5.19 (s, 2H), 4.37 (m, 1H), 3.13 (m, 2H), 2.73 (m, 2H), 1.99 (m, 2H), 1.70-1.52 (m, 2H). MS (ESI+) 452.06 (M+1H$^+$).

Example 15

6-(4-Chlorophenyl)-3-({2-[(1-methylpiperidin-4-yl)oxy]pyridin-4-yl}methyl)thieno[3,2-d]pyrimidin-4(3H)-one a) 2-[(1-Methylpiperidin-4-yl)oxy]isonicotinonitrile

1-Methylpiperidin-4-ol (0.457 g, 3.97 mmol) was dissolved in 5 mL of DMSO under argon and NaH (0.173 g, 3.97 mmol) was added. The reaction mixture was stirred at ambient temperature for 3 h and 30 min at 60° C. The mixture was allowed to cool and 2-chloro-4 pyridinecarbonitrile (0.500 g, 3.97 mmol) was added. The mixture was stirred for 2 h at ambient temperature and subsequently poured into 100 mL of water, extracted three times with EtOAc. The combined organic layer washed with water, dried over Na$_2$SO$_4$ and evaporated. The crude product was purified by preparative HPLC (Kromasil C8 50×250 mm, CH$_3$CN/0, 2% HOAc 5/95-50/50). The product was freeze dried from water. Yield: 0.250 g (32%). $^1$H NMR (500 MHz, CD$_3$OD) δ8.32 (d, 1H), 7.19 (dd, 1H), 7.12 (bs, 1H), 5.14 (m, 1H), 2.75 (m, 2H), 2.38 (m, 2H), 2.32 (s, 3H), 2.06 (m, 2H), 1.84 (m, 2H).

b) 1-{2-[(1-Methylpiperidin-4-yl)oxy]pyridin-4-yl}methanamine

2-[(1-Methylpiperidin-4-yl)oxy]isonicotinonitrile (0.250 g, 1.51 mmol, from step a above) was dissolved in 10 mL of ammonia saturated MeOH and 0.200 g Raney Nickel was added. The mixture was hydrogenated at 5 atm overnight. The mixture was filtered and evaporated to give 0.242 g (95%) of crude product which was used in the following step. $^1$H NMR (300 MHz, CD$_3$OD) δ 8.01 (d, 1H), 6.89 (d, 1H), 6.76 (bs, 1H), 5.00 (m, 1H), 3.77 (bs, 2H), 2.73 (m, 2H), 2.37 (m, 2H), 2.30 (s, 3H), 2.03 (m, 2H), 1.81 (m, 2H).

c) 6-(4-Chlorophenyl)-3-({2-[(1-methylpiperidin-4-yl)oxy]pyridin-4-yl}methyl)thieno[3,2-d]pyrimidin-4(3H)-one Methyl 5-(4-chlorophenyl)-3-{[(1E)-(dimethylamino)methylene]amino}thiophene-2-carboxylate (0.388 g, 1.20 mmol) and 1-{2-[(1-methylpiperidin-4-yl)oxy]pyridin-4-yl}methanamine (0.242 g, 1.09 mmol, from step b above) were mixed with 1.0 g of phenol and heated to 120° C. for 2 h. The mixture was purified by preparative HPLC (Kromasil C8-50×250 mm, CH$_3$CN/0, 1 M NH$_4$OAc 5/95-50/50 and CH$_3$CN/0, 2% HOAc 5/95-50/50). The product was freeze dried from water. Yield: 0.154 g (27%). $^1$H NMR (400 MHz, DMSO-d$_6$) δ 8.63 (s, 1H), 8.09 (d, 1H), 7.94 (s, 1H), 7.90 (m, 2H), 7.58 (m, 2H), 6.88 (m, 1H), 6.60 (bs, 1H), 5.20 (s, 2H), 4.95 (m, 1H), 2.60 (m, 2H), 2.15 (s, 3H), 2.12 (m, 2H), 1.92 (m, 2H), 1.62 (m, 2H). $^{13}$C NMR (100 MHz, DMSO-d$_6$) δ 163.7, 158.6, 156.8, 150.6, 149.4, 147.9, 135.1, 131.9, 130.0, 128.7, 122.5, 122.4, 116.1, 109.7, 53.4, 48.5, 46.5, 31.3. MS (ESI+) 467/469 (M+1H$^+$).

Example 16

6-(4-Chlorophenyl)-3-{3-[(1,4-dimethylpiperazin-2-yl)methoxy]benzyl}thieno[3,2-d]pyrimidin-4(3H)-one a) 3-[(1,4-Dimethylpiperazin-2-yl)methoxy]benzonitrile The title compound was synthesized according to Example 13a from (1,4-dimethylpiperazin-2-yl)methanol (0.500 g, 3.47 mmol), NaH (0.208 g, 5.20 mmol, 55% in oil) and 3-fluorobenzonitrile (0.441 g, 3.64 mmol) to give the title compound as an oil. Yield: 0.682 g (76%). $^1$H NMR (400 MHz, CDCl$_3$) δ 7.32-7.38 (m, 1H), 7.20-7.25 (m, 1H), 7.10-7.15 (m, 2H), 3.95-4.06 (m, 2H), 2.77-2.86 (m, 2H), 2.65-2.72 (m, 1H), 2.51-2.58 (m, 1H), 2.37-2.44 (m, 1H), 2.36 (s, 3H), 2.28 (s, 3H), 2.19-2.27 (m, 1H), 2.09-2.17 (m, 1H).

b) 1-{3-[(1,4-Dimethylpiperazin-2-yl)methoxy]phenyl}methanamine

The title compound was synthesized according to Example 13b from 3-[(1,4-dimethylpiperazin-2-yl)methoxy]benzonitrile (0.682 g, 2.78 mmol) to give the title compound as an oil. Yield: 0.636 g (92%). $^1$H NMR (400 MHz, CD$_3$OD) δ 7.21 (t, 1H, J=7.98 Hz), 6.87-6.93 (m, 2H), 6.78-6.83 (m, 1H), 3.94-4.00 (m, 1H), 4.04-4.09 (m, 1H), 3.73 (s, 2H), 2.90-2.96 (m, 1H), 2.73-2.86 (m, 2H), 2.51 (m, 1H), 2.34-2.44 (m, 4H), 2.20-2.31 (m, 4H), 2.10-2.17 (m, 1H).

c) 6-(4-Chlorophenyl)-3-{3-[(1,4-dimethylpiperazin-2-yl)methoxy]benzyl}thieno[3,2-d]pyrimidin-4(3H)-one The title compound was synthesized according to Example 13c from methyl 5-(4-chlorophenyl)-3-{[(1E)-(dimethylamino)methylene]amino}thiophene-2-carboxylate (0.427 g, 1.32 mmol) and 1-{3-[(1,4-dimethylpiperazin-2-yl)methoxy]phenyl}methanamine (0.300 g, 1.20 mmol) in MeOH (2 mL), the crude product was purified by flash chromatography using EtOAc:MeOH:TEA (100:10:1) to give the title compound. Yield: 0.315 g (48%). $^1$H NMR (400 MHz, CDCl$_3$) δ 8.07 (s, 1H), 7.58-7.62 (m, 2H), 7.38-7.42 (m, 2H), 7.45 (s, 1H), 7.22-7.27 (m, 1H), 6.82-6.93 (m, 3H), 5.16 (s, 2H), 3.91-4.01 (m, 2H), 2.76-2.87 (m, 2H), 2.66-2.73 (m, 1H), 2.47-2.55 (m, 1H), 2.36-2.44 (m, 1H), 2.34 (s, 3H), 2.27 (s, 3H), 2.09-2.27 (m, 2H). MS (ESI+) 495.01 (M+1H$^+$)

Example 17

6-(4-Chlorophenyl)-3-{3-[(1-methylpyrrolidin-3-yl)methoxy]benzyl}thieno[3,2-d]pyrimidin-4(3H)-one a) 3-[(1-Methylpyrrolidin-3-yl)methoxy]benzonitrile (1-Methylpyrrolidin-3-yl)methanol (0.500 g, 4.34 mmol) was dissolved in dry DMF (8 mL), cooled (<0° C.), NaH (0.260 g, 6.51 mmol, 55% in oil) added and stirred for 30 minutes. 3-Fluorobenzonitrile (0.552 g, 4.56 mmol) was added and the reaction mixture allowed to warm to r.t. over 1 h. Due to excessive foaming the reaction mixture was diluted with dry DMF to 20 mL and stirred over night at r.t. The reaction was quenched by addition of water portionwise, and the mixture was extracted with DCM. The organic phase was dried over a phase separator and concentrated in vacuo. The product was purified by flash chromatography using a step gradient of EtOAc:MeOH:TEA (100:10:2) in EtOAc to give the title compound as an oil. Yield: 0.573 g (58%). $^1$H NMR (400 MHz, CDCl$_3$) δ 7.30-7.35 (m, 1H), 7.18-7.22 (m, 1H), 7.09-7.12 (m, 1H), 7.07-7.09 (m, 1H), 3.86 (d, 2H, J=6.95 Hz), 2.54-2.67 (m, 3H), 2.40-2.51 (m, 2H), 2.33 (s, 3H), 2.00-2.10 (m, 1H), 1.51-1.61 (m, 1H).

b) 1-{3-[(1-Methylpyrrolidin-3-yl)methoxy]phenyl}methanamine

The title compound was synthesized according to Example 13b from 3-[(1-methylpyrrolidin-3-yl)methoxy]benzonitrile (0.573 g, 2.62 mmol) to give the title compound as an oil. Yield: 0.493 g (85%). $^1$H NMR (400 MHz, CD$_3$OD) δ 7.19 (t, 1H, J=7.88 Hz), 6.84-6.90 (m, 2H), 6.74-6.78 (m, 1H), 4.82 (s, 2H), 3.84-3.92 (m, 2H), 3.71 (s, 2H), 2.74-2.79 (m, 1H), 2.62-2.71 (m, 1H), 2.53-2.62 (m, 2H), 2.41-2.46 (m, 1H), 2.34 (s, 3H), 2.00-2.10 (m, 1H), 1.58-1.67 (m, 1H).

c) 6-(4-Chlorophenyl)-3-{3-[(1-methylpyrrolidin-3-yl)methoxy]benzyl}thieno[3,2-d]pyrimidin-4(3H)-one The title compound was synthesized according to Example 13c from methyl 5-(4-chlorophenyl)-3-{[(1E)-(dimethylamino)methylene]amino}thiophene-2-carboxylate (0.352 g, 1.09 mmol) and 1-{3-[(1-methylpyrrolidin-3-yl)methoxy]phenyl}methanamine (0.200 g, 0.91 mmol) in MeOH (2 mL) to give the title compound. Yield: 0.225 g (44%). $^1$H NMR (400 MHz, CDCl$_3$) δ 8.08 (s, 1H), 7.59-7.62 (m, 2H), 7.45 (s, 1H), 7.39-7.42 (m, 2H), 7.22-7.26 (m, 1H), 6.81-6.91 (m, 3H), 5.17 (s, 2H), 3.83 (d, 2H, J=6.9 Hz), 2.60-2.66 (m, 2H), 2.38-2.57 (m, 3H), 2.32 (s, 3H), 1.97-2.08 (m, 1H), 1.51-1.60 (m, 1H). MS (ESI+) 465.99 (M+1H$^+$)

Example 18

3-{3-[(3R)-1-Azabicyclo[2.2.2]oct-3-yloxy]benzyl}-6-(4-chlorophenyl)thieno[3,2-d]pyrimidin-4(3H)-one

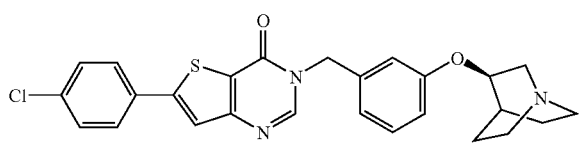

a) 3-[(3R)-1-Azabicyclo[2.2.2]oct-3-yloxy]benzonitrile

Prepared from (3R)-quinuclidin-3-ol (523 mg, 3.93 mmol) according to the procedure in example 12a. Purification by flash silica gel chromatography using a 40 g Biotage column with 100% EtOAc/MeOH/TEA 100:10:1 yielded the title compound as a colorless oil. Yield: 0.377 g (38%). $^1$H NMR (400 MHz, CDCl$_3$) δ 7.36-7.30 (m, 1H), 7.20 (dt, 1H, J=7.6 Hz, J=1.1 Hz), 7.08-7.04 (m, 2H), 4.37 (m, 1H), 3.27 (m, 1H), 2.99-2.70 (m, 5H), 2.11 (m, 1H), 1.91 (m, 1H), 1.74 (m, 1H), 1.60-1.49 (m, 1H), 1.38 (m, 1H).

b) 1-{3-[(3R)-1-Azabicyclo[2.2.2]oct-3-yloxy]phenyl}methanamine

Prepared from 3-[(3R)-1-azabicyclo[2.2.2]oct-3-yloxy]benzonitrile (377 mg, 1.65 mmol) according to the procedure in example 12b yielding the title compound as a colourless oil. Yield: 0.397 mg (100%). $^1$H NMR (400 MHz, CDCl$_3$) δ 7.23 (t, 1H, J=7.9 Hz), 6.87 (d, 1H, J=7.6 Hz), 6.84 (s, 1H), 6.73 (dd, 1H, J=8.1 Hz, J=2.3 Hz), 4.35 (m, 1H), 3.84 (s, 2H), 3.27 (m, 1H), 3.02-2.92 (m, 1H), 2.90-2.72 (m, 4H), 2.16-2.11 (m, 1H), 2.05-1.95 (m, 1H), 1.74 (m, 1H), 1.61-1.51 (m, 3H), 1.38 (m, 1H).

c) 3-{3-[(3R)-1-Azabicyclo[2.2.2]oct-3-yloxy]benzyl}-6-(4-chlorophenyl)thieno[3,2-d]pyrimidin-4(3H)-one Methyl 5-(4-chlorophenyl)-3-{[(1E)-(dimethylamino)methylene]amino}thiophene-2-carboxylate (177 mg, 0.548 mmol) and 1-{3-[(3R)-1-azabicyclo[2.2.2]oct-3-yloxy]phenyl}methanamine (140 mg, 0.603 mmol) were dissolved in MeOH (2 ml). The reaction was heated in a microwave at 120° C. for 30 minutes. The solvent was evaporated in vacuo. Purification by flash silica gel chromatography using a 40 g Biotage column with 100% EtOAc/MeOH/TEA 100:10:1 yielded the title compound as a white solid. Yield: 0.175 g (67%). $^1$H NMR (400 MHz, CDCl$_3$) δ 8.09 (s, 1H), 7.56 (m, 2H), 7.40 (s, 1H), 7.37 (m, 2H), 7.22 (t, 1H, J=7.9 Hz), 6.88 (d, 1H, J=7.9 Hz), 6.86 (m, 1H), 6.75 (dd, 1H, J=8.1 Hz, J=2.1 Hz), 5.15 (s, 2H), 4.33 (m, 1H), 3.24 (m, 1H), 2.97-2.88 (m, 1H), 2.86-2.69 (m, 4H), 2.08 (m, 1H), 1.99-1.88 (m, 1H), 1.70 (m, 1H), 1.57-1.47 (m, 1H), 1.34 (m, 1H). $^{13}$C NMR (100 MHz, CDCl$_3$) δ 158.3, 157.7, 157.1, 151.4, 148.2, 137.5, 135.7, 131.7, 130.4, 129.6, 127.8, 123.2, 121.0, 120.4, 115.8, 115.2, 73.6, 55.8, 49.5, 47.5, 46.8, 25.3, 24.6, 19.4. MS (ESI+) 478.00 (M+1H$^+$).

Example 19

6-(4-Chlorophenyl)-3-{3-[(1-isopropylpiperidin-4-yl)oxy]benzyl}thieno[3,2-d]pyrimidin-4(3H)-one, acetate salt a) 3-[(1-Isopropylpiperidin-4-yl)oxy]benzonitrile

Prepared from 1-isopropylpiperidin-4-ol (500 mg, 3.49 mmol) according to the procedure in example 12a. Purification by flash silica gel chromatography using a 40 g Biotage column with a gradient of 20-100% EtOAc/MeOH/TEA 100:10:1 in heptane yielded the title compound as a colorless oil. Yield: 0.581 g (68%). $^1$H NMR (400 MHz, CDCl$_3$) δ 7.35 (t, 1H, J=7.9 Hz), 7.21 (m, 1H), 7.16-7.10 (m, 2H), 4.31 (m, 1H), 2.82-2.70 (m, 3H), 2.40 (m, 2H), 2.06-1.96 (m, 2H), 1.81 (m, 2H), 1.06 (d, 6H, J=6.6 Hz).

b) 1-{3-[(1-Isopropylpiperidin-4-yl)oxy]phenyl}methanamine

Prepared from 3-[(1-isopropylpiperidin-4-yl)oxy]benzonitrile (581 mg, 2.380 mmol) according to the procedure in example 12b. Purification by reversed phase HPLC yielded the title compound as a colorless oil. Yield: 0.597 g (99%). $^1$H NMR (400 MHz, CDCl$_3$) δ 7.34 (t, 1H), 7.12 (s, 1H), 7.03-6.88 (m, 2H), 4.91 (s, 1H), 4.66 (m, 1H), 4.05 (br, 1H), 3.39-3.19 (m, 3H), 3.10 (m, 2H), 2.29-2.18 (m, 2H), 2.09-1.98 (m, 2H), 1.30 (d, 6H, J=6.6 Hz). MS (ESI+) 249.1 (M+1H$^+$).

c) 6-(4-Chlorophenyl)-3-{3-[(1-isopropylpiperidin-4-yl)oxy]benzyl}thieno[3,2-d]pyrimidin-4(3H)-one, acetate salt 1-{3-[(1-Isopropylpiperidin-4-yl)oxy]phenyl}methanamine (188 mg, 0.757 mmol) and methyl 5-(4-chlorophenyl)-3-{[(1E)-(dimethylamino)methylene]amino}thiophene-2-carboxylate (244 mg, 0.757 mmol) were dissolved in MeOH (2 ml). The reaction was heated in a microwave at 120° C. for 15 minutes, during which time a precipitate had been formed in the microwave vial. The precipitate was filtered off and washed with MeOH. The filtrate was purified by reversed phase HPLC yielding the title compound as a white solid. Yield: 37 mg (9%). $^1$H NMR (400 MHz, CDCl$_3$) δ 8.08 (s, 1H), 7.59 (m, 2H), 7.43 (s, 1H), 7.39 (m, 2H), 7.24 (t, 1H, J=7.9 Hz), 6.91-6.87 (m, 2H), 6.81 (dd, 1H, J=7.9 Hz, J=2.1 Hz), 5.15 (s, 2H), 4.40 (m, 1H, J=2.8 Hz), 3.06 (m, 1H, J=6.5 Hz), 2.87 (m, 2H), 2.75-2.67 (m, 2H), 2.14 (m, 2H), 1.97 (s, 2H), 1.90 (m, 2H), 1.13 (d, 6H, J=6.6 Hz). $^{13}$C NMR (100 MHz, CDCl$_3$) δ 177.0, 157.9, 157.7, 157.1, 151.6, 148.1, 137.5, 135.8, 131.7, 130.5, 129.9, 127.8, 123.3, 121.0, 120.7, 116.3, 115.5, 70.9, 55.3, 49.5, 44.4, 29.3, 23.3, 17.7. MS (ESI+) 494.0 (M+1H$^+$).

Example 20

6-(4-Chlorophenyl)-3-{3-[(1,3-dimethylpiperidin-3-yl)methoxy]benzyl}thieno[3,2-d]pyrimidin-4(3H)-one a) 3-[(1,3-Dimethylpiperidin-3-yl)methoxy]benzonitrile

To a solution of (1,3-dimethylpiperidin-3-yl)methanol (0.50 g, 3.5 mmol) in dry DMF (10 mL) at room temperature, 60% sodium hydride in oil (0.28 g, 7.0 mmol) was added. The reaction mixture was stirred at room temperature for 5 minutes and 3-fluoro benzonitrile (0.44 g, 3.7 mmol) was added. Due to excessive foaming the reaction mixture was diluted with dry DMF to 15 mL. The reaction mixture was then stirred at room temperature over night and quenched with water. The product was extracted with EtOAc and the organic layer was dried over MgSO$_4$ and concentrated in vacuo. The crude product was purified by flash chromatography using a gradient with EtOAc:MeOH:TEA (1:0.1:0.05) in EtOAc, which gave the product as a colorless oil. Yield: 0.53 g (59%). $^1$H NMR (400 MHz, CD$_3$OD) δ 7.41 (t, 1H, J=8.11 Hz), 7.20-7.27 (m, 3H), 3.89 (d, 1H, J=8.89 Hz), 3.82 (d, 1H, J=8.89 Hz), 2.21-2.51 (m, 3H), 2.19 (s, 3H), 2.12 (m, 1H), 1.54-1.67 (m, 3H), 1.21-1.30 (m, 1H), 1.07 (s, 3H).

b) 1-{3-[(1,3-Dimethylpiperidin-3-yl)methoxy]phenyl}methanamine

3-[(1,3-Dimethylpiperidin-3-yl)methoxy]benzonitrile (0.53 g, 2.2 mmol) was dissolved in MeOH (30 mL)/NH$_3$(sat) (0.05M) and hydrogenated over a Raney Nickel CatCart (30×4 mm) using the H-Cube system at 50 bar and 50° C. at a flow rate of 1 mL/min. LC-MS showed <100% conversion so the process was repeated. The reaction mixture was concentrated and dried in vacuo, which gave the product as a clear oil. Yield: 0.48 g (90%). $^1$H NMR (400 MHz, CD$_3$OD) δ 7.13 (t, 1H, J=8.12 Hz), 6.85 (s, 1H), 6.80 (d, 1H, J=7.61 Hz), 6.72 (d, 1H, J=7.61 Hz), 3.74 (m, 2H), 3.67 (s, 2H), 3.23 (s, 2H), 2.04-2.43 (m, 7H), 1.48-1.63 (m, 3H), 1.20 (m, 1H), 1.02 (s, 3H).

c) 6-(4-Chlorophenyl)-3-{3-[(1,3-dimethylpiperidin-3-yl)methoxy]benzyl}thieno[3,2-d]pyrimidin-4(3H)-one 5-(4-Chloro-phenyl)-3-(dimethylamino-methylene-amino)-thiophene-2-carboxylic acid methyl ester (0.16 g, 0.5 mmol), 1-{3-[(1,3-dimethylpiperidin-3-yl)methoxy]phenyl}methanamine (0.10 g, 0.4 mmol) in MeOH (2 mL) were heated by microwave at 120° C. for 20 minutes. The reaction mixture was allowed to cool to room temperature and the precipitate was filtered off and washed with MeOH to give the title compound as a solid. Yield: 0.12 g (49%). $^1$H NMR (400 MHz, CDCl$_3$) δ 8.09 (s, 1H), 7.61 (d, 2H, J=8.91 Hz), 7.45 (s, 1H), 7.43 (d, 2H, J=8.91 Hz), 7.21-7.25 (m, 1H), 6.84-6.92 (m, 3H), 5.17 (s, 2H), 3.72-3.83 (m, 2H), 2.34 (m, 2H), 2.18 (s, 3H), 2.06 (m, 1H), 1.49-1.64 (m, 4H), 1.18 (m, 1H), 1.04 (s, 3H). MS (ESI+) 494.06 (M+1H$^+$).

Example 21

2-(4-Chlorophenyl)-6-({6-[(1-methylpiperidin-4-yl)oxy]pyridin-2-yl}methyl)thieno[2,3-d]pyridazin-7(6H)-one a) 2-Bromo-6-({[tert-butyl(dimethyl)silyl]oxy}methyl)pyridine (6-Bromopyridin-2-yl)methanol (5.0 g, 26.6 mmol), DMAP (0.65 g, 5.3 mmol), tert-butyl(chloro)dimethylsilane (4.8 g, 31.9 mmol) and imidazole (2.3 g, 34.0 mmol) was mixed in DCM (100 mL) and stirred at room temperature overnight. The reaction mixture was washed with water (3×100 mL), dried over a phase separator and concentrated in vacuo to give the product as an oil. Yield: 8.3 g (103%) $^1$H NMR (400 MHz, CDCl$_3$) δ 7.55 (t, 1H, J=7.87 Hz), 7.46 (d, 1H, J=7.87 Hz), 7.32 (d, 1H, J=7.87 Hz), 0.94 (s, 9H), 0.10 (s, 6H).

b) tert-Butyl 4-{6-({[tert-butyl(dimethyl)silyl]oxy}methyl)pyridin-2-yl]oxy}piperidine-1-carboxylate 2-Bromo-6-({[tert-butyl(dimethyl)silyl]oxy}methyl)pyridine (2.7 g, 7.51 mmol), tert-butyl 4-hydroxypiperidine-1-carboxylate (1.5 g, 7.51 mmol), palladium(II) acetate (0.034 g, 0.15 mmol), biphenyl-2-yl(di-tert-butyl)phosphine (0.056 g, 0.19 mmol) and cesium carbonate (4.9 g, 15.0 mmol) were mixed in a 40 mL vial and dry toluene (25 ml) was added. The vial was then briefly evacuated and backfilled with N$_2$ five times, and the reaction vessel was heated at 100° C. under N$_2$ atmosphere for 24 hours. The reaction mixture was cooled to room temperature. The reaction mixture was diluted with toluene (100 mL), washed with water, the organics dried over MgSO$_4$ and concentrated in vacuo. Purification by flash chromatography using a gradient with toluene:EtOAc (98:2-80:20), gave the product as an oil. Yield: 1.1 g (33%). $^1$H NMR (400 MHz, CDCl$_3$) δ 7.44 (t, 1H, J=7.82 Hz), 6.89 (d, 1H, J=7.30 Hz), 6.43 (d, 1H, J=8.34 Hz), 5.04-5.11 (m, 1H), 4.56 (s, 2H), 3.58-3.68 (m, 2H), 3.12-3.21 (m, 2H), 1.78-1.87 (m, 2H), 1.53-1.64 (m, 2H), 1.35 (s, 9H), 0.84 (s, 9H), 0.00 (s, 6H). MS (ESI+) 423.24 (M+1H$^+$).

c) tert-Butyl 4-{[6-(hydroxymethyl)pyridin-2-yl]oxy}piperidine-1-carboxylate To a solution of tert-butyl 4-{[6-({[tert-butyl(dimethyl)silyl]oxy}methyl)pyridin-2-yl]oxy}piperidine-1-carboxylate (0.50 g, 1.18 mmol) in THF (8 mL) was added tetrabutylammonium fluoride (1.78 mL, 1.0 M in THF, 1.78 mmol). The resulting mixture was stirred at room temperature for 1 hour, concentrated and purified by flash chromatography using a gradient run from 5-100% EtOAc in toluene. The selected fractions were concentrated in vacuo to give the product as a clear oil. Yield: 0.34 g (93%). $^1$H NMR (400 MHz, CDCl$_3$) δ 7.54 (t, 1H, J=7.66 Hz), 6.78 (d, 1H, J=7.26 Hz), 6.59 (d, 1H, J=8.16 Hz), 5.15-5.26 (m, 1H), 4.62 (s, 2H), 3.66-3.77 (m, 2H), 3.25-3.37 (m, 3H), 1.89-1.99 (m, 2H), 1.59-1.82 (m, 2H), 1.45 (s, 9H).

d) tert-Butyl 4-[(6-{[(methylsulfonyl)oxy]methyl}pyridin-2-yl)oxy]piperidine-1-carboxylate tert-Butyl 4-{[6-(hydroxymethyl)pyridin-2-yl]oxy}piperidine-1-carboxylate (0.34 g, 1.10 mmol) and methanesulfonyl chloride (0.13 mL, 1.64 mmol) were dissolved in DCM (15 mL) and stirred at 0° C. (ice bath). DIPEA (0.57 mL, 3.29 mmol) was added to the reaction mixture and stirred for 2 hours. The resulting mixture washed with water (2×15 mL), dried over a phase separator, concentrated in vacuo and was used directly in the next step.

e) tert-Butyl 4-[(6-{[2-(4-chlorophenyl)-7-oxothieno[2,3-d]pyridazin-6(7H)-yl]methyl}pyridin-2-yl)oxy]piperidine-1-carboxylate To a stirred solution of 2-(4-chlorophenyl)thieno[2,3-d]pyridazin-7(6H)-one (0.32 g, 1.22 mmol) in DMF (10 mL) was added 60% sodium hydride in oil (0.06 g, 1.34 mmol, 55%). Stirred for 10 minutes under N$_2$ atmosphere before addition of tert-butyl 4-[(6-{[(methylsulfonyl)oxy]methyl}pyridin-2-yl)oxy]piperidine-1-carboxylate (crude product from step d) dissolved in DMF (10 mL). The resulting mixture was stirred for 18 hours at room temperature followed by prep-HPLC purification to give the product. Yield: 0.22 g (32% over two steps). $^1$H NMR (400 MHz, CDCl$_3$) δ 8.19 (s, 1H), 7.60-7.64 (m, 2H), 7.40-7.51 (m, 4H), 6.75 (d, 1H, J=7.28 Hz), 6.54 (d, 1H, J=8.24 Hz), 5.47 (s, 2H), 4.90-4.99 (m, 1H), 3.58-3.70 (m, 2H), 2.94-3.04 (m, 2H), 1.73-1.82 (m, 2H), 1.47-1.60 (m, 2H), 1.39 (s, 9H). $^{13}$C NMR (100 MHz, CDCl$_3$) δ 162.9, 157.3, 155.1, 153.7, 152.5, 140.3, 139.5, 136.4, 136.1, 133.1, 131.2, 129.8, 128.3, 118.9, 114.2, 110.3, 79.7, 70.6, 55.7, 41.3, 30.8, 28.7.

f) 2-(4-Chlorophenyl)-6-{[6-(piperidin-4-yloxy)pyridin-2-yl]methyl}thieno[2,3-d]pyridazin-7(6H)-one tert-butyl 4-[(6-{[2-(4-chlorophenyl)-7-oxothieno[2,3-d]pyridazin-6(7H)-yl]methyl}pyridin-2-yl)oxy]piperidine-1- carboxylate (0.22 g, 0.39 mmol) was dissolved in DCM/TFA 5:1 (6 mL) and stirred for 1 hour. The reaction mixture was co-evaporated with toluene, dissolved in DCM (20 mL) and washed with sat. NaHCO$_3$(aq.)/water 1:1 (30 mL). The resulting water phase was extracted with DCM (3×20 mL). The combined organics were dried over a phase separator and concentrated in vacuo to give the product. Yield: 0.16 g (89%). MS (ESI+) 453.06 (M+1H$^+$).

g) 2-(4-Chlorophenyl)-6-({6-[(1-methylpiperidin-4-yl)oxy]pyridin-2-yl}methyl)thieno[2,3-d]pyridazin-7(6H)-one To a solution of 2-(4-chlorophenyl)-6-{[6-(piperidin-4-yloxy)pyridin-2-yl]methyl}thieno[2,3-d]pyridazin-7(6H)-one (0.16 g, 0.34 mmol) in DCM/MeOH (1:1, 10 mL) was added (polystyrylmethyl)trimethylammonium cyanoborohydride (0.25 g, 1.03 mmol), 36% aq. formaldehyde (0.05 mL, 0.69 mmol) and acetic acid (one drop). After 3 hours of stirring one additional amount of (polystyrylmethyl)trimethylammonium cyanoborohydride, formaldehyde and acetic acid added to the reaction mixture and stirred for two hours. The reaction mixture was filtrated, concentrated in vacuo and purified by flash chromatography using a gradient with EtOAc:MeOH:TEA (1:0.1:0.05) in n-heptane, which gave the product. Yield: 0.084 g (52%). $^1$H NMR (400 MHz, CDCl$_3$) δ 8.19 (s, 1H), 7.57-7.64 (m, 2H), 7.30-7.49 (m, 4H), 6.71 (d, 1H, J=7.31 Hz), 6.52 (d, 1H, J=8.16 Hz), 5.47 (s, 2H), 4.69-4.79 (m, 1H), 2.49-2.58 (m, 2H), 2.13 (s, 3H), 1.87-1.99 (m, 2H), 1.75-1.84 (m, 2H), 1.58-1.69 (m, 2H). $^{13}$C NMR (100 MHz, CDCl$_3$) δ 163.0, 157.4, 153.5, 152.3, 140.3, 139.3, 136.4, 136.0, 133.1, 131.3, 129.8, 128.1, 113.8, 110.1, 70.5, 55.6, 53.3, 46.4, 31.0 MS (ESI+) 467.08 (M+1H$^+$).

Example 22

2-(4-Methoxyphenyl)-6-[(6-{[(2S)-1-methylpiperidin-2-yl]methoxy}pyridin-2-yl)methyl]thieno[2,3-d]pyridazin-7(6H)-one a) tert-Butyl (2S)-2-({[6-({[tert-butyl(dimethyl)silyl]oxy}methyl)pyridin-2-yl]oxy}methyl)piperidine-1-carboxylate 2-Bromo-6-({[tert-butyl(dimethyl)silyl]oxy}methyl)pyridine (702 mg, 2.32 mmol, from Example 21a), tert-butyl (2S)-2-(hydroxymethyl)piperidine-1-carboxylate (500 mg, 2.32 mmol), Pd(OAc)$_2$ (26 mg, 0.116 mmol), 2-(di-t-butylphosphino)biphenyl (42 mg, 0.139 mmol) and Cs$_2$(CO$_3$) (1.51 g, 4.64 mmol) were mixed in toluene (20 ml). The reaction was stirred under an N$_2$ atmosphere and heated to 100° C. on an oil bath for 24 h. The solvent was evaporated in vacuo and the residue separated between EtOAc (250 ml) and water (250 ml). The organic phase washed with water (250 ml) and the combined aqueous phases were extracted with EtOAc (250 ml). The combined EtOAc phases were dried over Na$_2$SO$_4$ (s), filtered and evaporated in vacuo. Purification by silica gel flash chromatography using a 40+M Biotage column with a gradient of 5-20% EtOAc in heptane yielded the title compound as a colorless oil. Yield: 729 mg (72%). $^1$H NMR (400 MHz, CDCl$_3$) δ 7.43 (t, 1H, J=7.8 Hz), 6.91 (d, 1H, J=7.3 Hz), 6.44 (d, 1H, J=8.2 Hz), 4.57 (s, 2H), 4.48 (m, 1H), 4.25 (d, 2H, J=7.4 Hz), 3.91 (d, 1H, J=11.6 Hz), 2.76 (dt, 1H, J=13.3 Hz, J=2.0 Hz), 1.69 (d, 1H, J=12.0 Hz), 1.57-1.37 (m, 5H), 1.27 (s, 9H), 0.84 (s, 9H), 0.00 (s, 6H).

b) tert-Butyl (2S)-2-({[6-(hydroxymethyl)pyridin-2-yl]oxy}methyl)piperidine-1-carboxylate tert-Butyl (2S)-2-({[6-({[tert-butyl(dimethyl)silyl]oxy}methyl)pyridin-2-yl]oxy}methyl)piperidine-1-carboxylate (729 mg, 1.67 mmol) was dissolved in THF (10 ml) and tetrabutylammonium fluoride (1.0 M in THF, 2.5 ml, 2.5 mmol) added. The reaction stirred at rt. for 1 h and the solvent removed in vacuo. Purification by silica gel flash chromatography using a Biotage 25+M column with EtOAc/heptane 1:1 yielded the title compound as a colorless oil. Yield: 520 mg (97%). $^1$H NMR (400 MHz, CDCl$_3$) δ 7.52 (t, 1H, J=7.8 Hz), 6.76 (d, 1H, J=7.3 Hz), 6.59 (d, 1H, J=8.2 Hz), 4.68-4.61 (m, 3H), 4.50 (dd, 1H, J=10.6 Hz, J=7.2 Hz), 4.32 (dd, 1H, J=10.2 Hz, J=7.7 Hz), 4.01 (d, 1H, J=11.6 Hz), 3.59 (bs, 1H), 2.86 (dt, 1H, J=13.1 Hz, J=2.3 Hz), 1.81 (d, 1H, J=11.9 Hz), 1.67-1.49 (m, 5H), 1.38 (s, 9H).

c) tert-Butyl (2S)-2-{[(6-{[(methylsulfonyl)oxy]methyl}pyridin-2-yl)oxy]methyl}piperidine-1-carboxylate tert-Butyl (2S)-2-({[6-(hydroxymethyl)pyridin-2-yl]oxy}methyl)piperidine-1-carboxylate (520 mg, 1.61 mmol) and DIPEA (0.842 ml, 4.84 mmol) dissolved in DCM (10 ml) was cooled using an ice bath. Methanesulfonyl chloride (0.191 ml, 2.419 mmol) was added and the reaction stirred for 2 h. DCM (150 ml) and water (150 ml) were added and the phases separated. The organic phase washed with water (150 ml), dried through a phase separator and evaporated in vacuo, yielding the title compound as a light yellow oil (672 mg (104%)) which was used directly in the next step without further purification. MS (ESI+) 401.20 (M+1H$^+$)

d) tert-Butyl (2S)-2-{[(6-{[2-(4-methoxyphenyl)-7-oxothieno[2,3-d]pyridazin-6(7H)-yl]methyl}pyridin-2-yl)oxy]methyl}piperidine-1-carboxylate To a solution of 2-(4-methoxyphenyl)thieno[2,3-d]pyridazin-7(6H)-one (455 mg, 1.76 mmol) in DMF (5 ml), was added NaH 60% (110 mg, 2.52 mmol) in small portions. The mixture was stirred at rt. for 10 min before addition of tert-butyl (2S)-2-{[(6-{[(methylsulfonyl)oxy]methyl}pyridin-2-yl)oxy]methyl}piperidine-1-carboxylate (672 mg, 1.68 mmol) dissolved in DMF (3 ml). The reaction was stirred at rt. for 16 h, water (150 ml) and DCM (150 ml) added and the phases separated. The aqueous phase was extracted with DCM (150 ml). The combined organic phases were dried through a phase separator and evaporated in vacuo. Purification by silica gel flash chromatography using a 40+M Biotage column with a gradient of 30-100% EtOAc in heptane yielded the title compound as a light yellow solid. Yield: 354 mg (36%). $^1$H NMR (400 MHz, CDCl$_3$) δ 8.17 (s, 1H), 7.61 (m, 2H), 7.46 (t, 1H, J=7.8 Hz), 7.34 (s, 1H), 6.96 (m, 2H), 6.71 (d, 1H, J=7.3 Hz), 6.55 (d, 1H, J=8.2 Hz), 5.47 (s, 2H), 4.50 (m, 1H), 4.30 (m, 2H), 3.94 (d, 1H, J=10.7 Hz), 3.85 (s, 3H), 2.74 (t, 1H, J=12.2 Hz), 1.67-1.20 (m, 15H). MS (ESI+) 563.30 (M+1H$^+$)

e) 2-(4-Methoxyphenyl)-6-({6-[(2S)-piperidin-2-ylmethoxy]pyridin-2-yl}methyl)thieno[2,3-d]pyridazin-7(6H)-one tert-Butyl (2S)-2-{[(6-{[2-(4-methoxyphenyl)-7-oxothieno[2,3-d]pyridazin-6(7H)-yl]methyl}pyridin-2-yl)oxy]methyl}piperidine-1-carboxylate (354 mg, 0.629 mmol) was dissolved in DCM (7 ml) and TFA (1 ml) was added. The reaction was stirred at rt. for 30 min and the solvent evaporated in vacuo. To the resultant oil was added DCM (100 ml) and 5% $Na_2CO_3$ (aq) (100 ml), the phases separated and the aqueous phase extracted with DCM (100 ml). The combined organics were dried through a phase separator and evaporated in vacuo yielding the title compound as a light yellow solid. Yield: 290 mg (100%). MS (ESI+) 463.23 (M+1H$^+$)

f) 2-(4-Methoxyphenyl)-6-[(6-{[(2S)-1-methylpiperidin-2-yl]methoxy}pyridin-2-yl)methyl]thieno[2,3-d]pyridazin-7(6H)-one To a solution of 2-(4-methoxyphenyl)-6-({6-[(2S)-piperidin-2-ylmethoxy]pyridin-2-yl}methyl)thieno[2,3-d]pyridazin-7(6H)-one (290 mg, 0.627 mmol) in MeOH/DCM 1:1(15 ml), were added (polystyrylmethyl)trimethylammonium cyanoborohydride (460 mg, 1.881 mmol, 4.1 mmol/g) and formaldehyde (100 μl, 1.25 mmol) followed by AcOH (one drop). After stirring at rt. for 3 h the resin was filtered off and washed with MeOH. The filtrate was collected and evaporated in vacuo. Purification by silica gel flash chromatography using a 25+M Biotage column with EtOAc/MeOH/TEA 100:10:1 gave the title compound as a light yellow solid. Yield: 201 mg (67%). $^1$H NMR (400 MHz, CDCl$_3$) δ 8.18 (s, 1H), 7.61 (m, 2H), 7.47 (t, 1H, J=7.8 Hz), 7.34 (s, 1H), 6.96 (m, 2H), 6.71 (d, 1H, J=7.3 Hz), 6.63 (d, 1H, J=8.3 Hz), 5.47 (s, 2H), 4.26 (m, 2H), 3.84 (s, 3H), 2.81 (dt, 1H, J=11.5 Hz, J=3.1 Hz), 2.27 (s, 3H), 2.11 (m, 1H), 2.02 (m, 1H), 1.66 (m, 2H), 1.54 (m, 2H), 1.42 (m, 1H), 1.20 (m, 1H). $^{13}$C NMR (400 MHz, CDCl$_3$) δ 163.7, 161.1, 157.4, 153.94, 153.88, 140.5, 139.2, 135.4, 133.3, 128.3, 125.5, 117.2, 114.9, 114.2, 110.1, 67.8, 63.1, 57.5, 55.8, 55.6, 43.6, 29.5, 26.0, 24.3. MS (ESI+) 477.25 (M+1H$^+$)

Example 23

6-(4-Chlorophenyl)-3-[(6-{[1-(2-hydroxyethyl)piperidin-4-yl]oxy}pyridin-2-yl)methyl]thieno[3,2-d]pyrimidin-4(3H)-one a) tert-Butyl 4-[(6-cyanopyridin-2-yl)oxy]piperidine-1-carboxylate 6-Bromo-2-pyridinecarbonitrile (1.00 g, 5.46 mmol), tert-butyl 4-hydroxypiperidine-1-carboxylate (1.10 g, 5.46 mmol), Pd(OAc)$_2$ (61 mg, 0.27 mmol), 2-(di-t-butylphosphino)biphenyl (98 mg, 0.328 mmol) and Cs$_2$CO$_3$ (3.56 g, 10.93 mmol) were mixed in toluene (20 ml). The reaction was stirred under an N$_2$ atmosphere and heated to 130° C. on an oil bath for 24 h. The solvent was evaporated in vacuo and the remaining separated between EtOAc (500 ml) and water (500 ml). The aqueous phase was extracted with EtOAc (500 ml). The combined organic phases were washed with water (500 ml), dried with Na$_2$SO$_4$ (s), filtered and evaporated in vacuo. Purification by silica gel flash chromatography using a 40 g Biotage column with a gradient of 5-30% EtOAc in heptane giving the title compound as a white solid. Yield: 605 mg (37%). $^1$H NMR (400 MHz, CDCl$_3$) δ 7.63 (dd, 1H, J=8.4 Hz, J=7.3 Hz), 7.25 (d, 1H, J=7.3 Hz), 6.90 (d, 1H, J=8.4 Hz), 5.21 (m, 1H), 3.74 (m, 2H), 3.25 (m, 2H), 1.95 (m, 2H), 1.68 (m, 2H), 1.44 (s, 9H).

b) tert-Butyl 4-{[6-(aminomethyl)pyridin-2-yl]oxy}piperidine-1-carboxylate

Prepared from tert-butyl 4-[(6-cyanopyridin-2-yl)oxy]piperidine-1-carboxylate (605 mg, 1.99 mmol) according to the procedure in Example 12b. Evaporation in vacuo yielded the title compound as a colorless oil (629 mg (103%)) which was used directly in the next step without further purification. $^1$H NMR (400 MHz, CDCl$_3$) δ 7.54 (t, 1H, J=7.7 Hz), 6.82 (d, 1H, J=7.1 Hz), 6.62 (d, 1H, J=8.2 Hz), 5.38 (m, 1H), 4.02 (s, 2H), 3.71 (m, 2H), 3.32 (m, 2H), 1.93 (m, 2H), 1.69 (m, 2H), 1.46 (s, 9H). MS (ESI+) 308.18 (M+1H$^+$)

c) tert-Butyl 4-[(6-{[6-(4-chlorophenyl)-4-oxothieno[3,2-d]pyrimidin-3(4H)-yl]methyl}pyridin-2-yl)oxy]piperidine-1-carboxylate Prepared from tert-butyl 4-{[6-(aminomethyl)pyridin-2-yl]oxy}piperidine-1-carboxylate (629 mg, 2.05 mmol) and 5-(4-chloro-phenyl)-3-(dimethylamino-methyleneamino)-thiophene-2-carboxylic acid methyl ester (662 mg, 2.05 mmol) according to the procedure in Example 14c. Purification by silica gel flash chromatography using a 40+M Biotage column with a gradient of 10-100% EtOAc in heptane yielded the title compound as a colorless solid. Yield: 679 mg (60%). $^1$H NMR (400 MHz, CDCl$_3$) δ 8.27 (s, 1H), 7.60 (m, 2H), 7.53 (t, 1H, J=7.7 Hz), 7.46 (s, 1H), 7.39 (m, 2H), 6.95 (d, 1H, J=7.2 Hz), 6.60 (d, 1H, J=8.2 Hz), 5.18 (s, 2H), 4.96 (m, 1H), 3.66 (m, 2H), 3.09 (m, 2H), 1.78 (m, 2H), 1.56 (m, 2H), 1.41 (s, 9H).

d) 6-(4-Chlorophenyl)-3-{[6-(piperidin-4-yloxy)pyridin-2-yl]methyl}thieno[3,2-d]pyrimidin-4(3H)-one tert-Butyl 4-[(6-{[6-(4-chlorophenyl)-4-oxothieno[3,2-d]pyrimidin-3(4H)-yl]methyl}pyridin-2-yl)oxy]piperidine-1-carboxylate (679 mg, 1.23 mmol) was dissolved in DCM (5 ml) and TFA (1 ml) added. The reaction was stirred at rt. for 40 minutes. DCM (150 ml) and sat. Na$_2$CO$_3$ (aq) (150 ml) were added, the phases separated and the aqueous phase extracted with DCM (150 ml). The combined organics were dried through a phase separator and evaporated in vacuo to yield the title compound as a colorless oil. Yield: 550 mg (99%). $^1$H NMR (400 MHz, CDCl$_3$) δ 8.29 (s, 1H), 7.63 (m, 2H), 7.55 (dd, 1H, J=8.0 Hz, J=7.4 Hz), 7.48 (s, 1H), 7.42 (m, 2H), 6.95 (d, 1H, J=7.2 Hz), 6.61 (d, 1H, J=8.2 Hz), 5.20 (s, 2H), 4.90 (m, 1H), 3.01 (m, 2H), 2.61 (m, 2H), 1.87 (m, 2H), 1.60-1.46 (m, 3H). $^{13}$C NMR (400 MHz, CDCl$_3$) δ 163.2, 157.9, 157.1, 151.6, 151.4, 149.3, 139.8, 135.8, 131.8, 129.6, 127.8, 123.1, 121.0, 115.0, 111.3, 71.9, 50.2, 44.4, 32.6. MS (ESI+) 453.00 (M+1H$^+$)

e) 6-(4-Chlorophenyl)-3-[(6-{[1-(2-hydroxyethyl)piperidin-4-yl]oxy}pyridin-2-yl)methyl]thieno[3,2-d]pyrimidin-4(3H)-one 6-(4-Chlorophenyl)-3-{[6-(piperidin-4-yloxy)pyridin-2-yl]methyl}thieno[3,2-d]pyrimidin-4(3H)-one (165 mg, 0.364 mmol) was dissolved in MeOH (8 ml) and cooled to 0° C. Ethylene oxide was bubbled through the solution for about 3 minutes and the reaction stirred at 0° C. for 5 h. The solvent was evaporated in vacuo and stored in a freezer for 2 d. The oil was redissolved in MeOH (8 ml), cooled to 0° C. and ethylene oxide bubbled through. The reaction was stirred for 6 h and then evaporated in vacuo. Purification by silica gel flash chromatography using a 25+M Biotage column with 100% EtOAc/MeOH/TEA 100:10:1 yielded the title compound as a white solid. Yield: 87 mg (48%). $^1$H NMR (400 MHz, CDCl$_3$) δ 8.28 (s, 1H), 7.63 (m, 2H), 7.55 (dd, 1H, J=8.2 Hz, J=7.4 Hz), 7.49 (s, 1H), 7.43 (m, 2H), 6.96 (d, 1H, J=7.2 Hz), 6.61 (d, 1H, J=8.2 Hz), 5.21 (s, 2H), 4.86 (m, 1H), 3.56 (t, 2H, J=5.3 Hz), 2.72 (m, 2H), 2.50 (t, 2H, J=5.3 Hz), 2.25 (t, 2H, J=9.3 Hz), 1.90 (m, 2H), 1.69 (m, 2H). $^{13}$C NMR (400 MHz, CDCl$_3$) δ 163.2, 157.9, 157.1, 151.6, 151.5, 149.3, 139.8, 135.9, 131.8, 129.7, 127.8, 123.1, 121.0, 115.1, 111.2, 70.9, 59.3, 58.0, 50.8 50.2, 30.9. MS (ESI+) 497.10 (M+1H$^+$)

Example 24

6-(4-Chlorophenyl)-3-(3-{[(2S)-1-methylpyrrolidin-2-yl]methoxy}benzyl)thieno[3,2-d]pyrimidin-4(3H)-one a) 3-{[(2S)-1-methylpyrrolidin-2-yl]methoxy}benzonitrile The title compound was synthesised using the same method as described for Example 20a using the reagents. [(2S)-1-methylpyrrolidin-2-yl]methanol (0.50 g, 4.3 mmol), 60% sodium hydride in oil (0.35 g, 8.7 mmol) and 3-fluoro benzonitrile (0.44 g, 3.7 mmol) which gave the product as an oil. Yield: 0.65 g (82%). $^1$H NMR (400 MHz, CDCl$_3$) δ 7.98 (s, 1H), 7.29-7.36 (m, 1H), 7.17-7.22 (m, 1H), 7.08-7.13 (m, 1H), 3.91-3.97 (m, 1H), 3.83-3.90 (m, 1H), 3.04-3.14 (m, 1H), 2.58-2.67 (m, 1H), 2.44 (s, 3H), 2.23-2.32 (m, 1H), 1.94-2.06 (m, 1H), 1.63-1.87 (m, 3H).

b) 1-(3-{[(2S)-1-methylpyrrolidin-2-yl]methoxy}phenyl)methanamine

The title compound was synthesised using the same method as described for Example 20b, to give the product as an oil. Yield: 0.25 g (82%). $^1$H NMR (400 MHz, CD$_3$OD) δ 7.13-7.19 (m 1H), 6.81-6.89 (m, 2H), 6.72-6.77 (m, 1H), 3.88-3.99 (m, 2H), 3.69 (s, 2H), 2.97-3.05 (m, 1H), 2.60-2.70 (m, 1H), 2.43 (s, 3H), 2.23-2.33 (m, 1H), 1.95-2.08 (m, 1H), 1.70-1.81 (m, 2H), 1.57-1.70 (m, 1H).

c) 6-(4-Chlorophenyl)-3-(3-{[(2S)-1-methylpyrrolidin-2-yl]methoxy}benzyl)thieno[3,2-d]pyrimidin-4(3H)-one The title compound was synthesised using the same method as described for Example 20c using the reagents 5-(4-Chloro-phenyl)-3-(dimethylamino-methyleneamino)-thiophene-2-carboxylic acid methyl ester (0.176 g, 0.55 mmol) and 1-(3-{[(2S)-1-methylpyrrolidin-2-yl]methoxy}phenyl)methanamine (0.10 g, 0.45 mmol). Purification by prep-HPLC gave the product as a solid. Yield: 0.22 g (41%). $^1$H NMR (400 MHz, CD$_3$OD) δ 8.08 (s, 1H), 7.58-7.64 (m, 2H), 7.38-7.46 (m, 3H), 7.21-7.27 (m, 1H), 6.82-6.94 (m, 3H), 5.17 (s, 2H), 3.90-3.99 (m, 1H), 3.79-3.87 (m, 1H), 3.03-3.13 (m, 1H), 2.54-2.66 (m, 1H), 2.43 (s, 3H), 2.22-2.32 (m, 1H), 1.92-2.06 (m, 1H), 1.64-1.88 (m, 3H). MS (ESI+) 466.12 (M+1H$^+$).

Example 25

2-(4-Chlorophenyl)-6-[(6-{[(2R)-1-methylpyrrolidin-2-yl]methoxy}pyridin-2-yl)methyl]thieno[2,3-d]pyridazin-7(6H)-one a) tert-Butyl (2R)-2-({[6-({[tert-butyl(dimethyl)silyl]oxy}methyl)pyridin-2-yl]oxy}methyl)pyrrolidine-1-carboxylate 2-Bromo-6-({[tert-butyl(dimethyl)silyl]oxy}methyl)pyridine (1.0 g, 3.3 mmol, from Example 21a), tert-butyl (2R)-2-(hydroxymethyl)pyrrolidine-1-carboxylate (0.67 g, 3.3 mmol), Pd(OAc)$_2$ (14.8 mg, 0.066 mmol), 2'-(di-tert-butylphosphino)-N,N-dimethylbiphenyl-2-amine (28 mg, 0.083 mmol), Cs$_2$CO$_3$ (2.15 g, 6.6 mmol) and toluene (10 mL) were mixed, degassed and stirred at 100° C. under a nitrogen atmosphere. After 24 h, additional portions of Pd(OAc)$_2$ (14.8 mg, 0.066 mmol) and 2'-(di-tert-butylphosphino)-N,N-dimethylbiphenyl-2-amine (28 mg, 0.083 mmol) were added and the reaction mixture was stirred for another 24 h. H$_2$O and DCM were added and the organic phase was separated and evaporated. The residue was purified by flash chromatography using a gradient of EtOAc/heptane to give the title compound. Yield: 604 mg (43%). $^1$H NMR (400 MHz, CDCl$_3$) δ 7.56 (t, J=8.2 Hz, 1H), 7.05 (d, J=7.0 Hz, 1H), 6.58 (d, J=8.8 Hz, 1H), 4.69 (s, 2H), 4.41-4.30 (m, 1H), 4.22-4.08 (m, 2H), 3.46-3.28 (m, 2H), 2.03-1.90 (m, 3H), 1.88-1.78 (m, 1H), 1.46 (s, 9H), 0.96 (s, 9H), 0.11 (s, 6H). MS (ESI+) 445.4 (M+1Na$^+$).

b) tert-Butyl (2R)-2-({[6-(hydroxymethyl)pyridin-2-yl]oxy}methyl)pyrrolidine-1-carboxylate tert-Butyl (2R)-2-({[6-({[tert-butyl(dimethyl)silyl]oxy}methyl)pyridin-2-yl]oxy}methyl)pyrrolidine-1-carboxylate (604 mg, 1.4 mmol) was dissolved in THF (5 mL) and tetrabutylammonium fluoride (2.1 mL, 1.0M in THF, 2.1 mmol) was added. The reaction mixture was stirred 1 h. The organic solvent was evaporated and the residue purified by flash chromatography using a gradient of EtOAc/heptane to give the title compound as a clear oil. Yield: 430 mg (97%). MS (ESI+) 309.3 (M+1H+).

c) tert-Butyl (2R)-2-{[(6-{[(methylsulfonyl)oxy]methyl}pyridin-2-yl)oxy]methyl}pyrrolidine-1-carboxylate tert-Butyl (2R)-2-({[6-(hydroxymethyl)pyridin-2-yl]oxy}methyl)pyrrolidine-1-carboxylate (430 mg, 1.4 mmol) was dissolved in DCM (15 mL) and MsCl (240 mg, 2.1 mmol) was added. The reaction mixture was cooled to 0° C. and DIPEA (0.72 mL, 4.1 mmol) were added. The reaction mixture was stirred 2 h at ambient temperature and water was added. The organic phase was separated and evaporated. The residue was purified by flash chromatography using a gradient of EtOAc/heptane to give the title compound as a clear oil. Yield: 420 mg (78%). $^1$H NMR (399.961 MHz, CDCl$_3$) δ 7.61 (t, J=8.2 Hz, 1H), 7.01 (d, J=6.6 Hz, 1H), 6.72 (d, J=8.5 Hz, 1H), 5.20 (s, 2H), 4.49-4.30 (m, 1H), 4.27-4.06 (m, 2H), 3.50-3.27 (m, 2H), 3.07 (s, 3H), 2.04-1.90 (m, 3H), 1.90-1.81 (m, 1H), 1.46 (s, 9H). MS (ESI+) 387.2 (M+1H+).

d) tert-Butyl (2R)-2-{[(6-{[2-(4-chlorophenyl)-7-oxothieno[2,3-d]pyridazin-6(7H)-yl]methyl}pyridin-2-yl)oxy]methyl}pyrrolidine-1-carboxylate 2-(4-Chlorophenyl)thieno[2,3-d]pyridazin-7(6H)-one (285 mg, 1.1 mmol) was added to dry DMF (5 mL) and NaH (71 mg, 55% in mineral oil, 1.6 mmol) was added in small potions and stirred 10 min. tert-butyl (2R)-2-{[(6-{[(methylsulfonyl)oxy]methyl}pyridin-2-yl)oxy]methyl}pyrrolidine-1-carboxylate (420 mg, 1.1 mmol) dissolved in dry DMF (3 mL) was added drop wise and the reaction mixture was stirred at ambient temperature for 3 h. Water was added and the aqueous phase was extracted three times with DCM. The organic phase was evaporated and purified by flash chromatography using a gradient of EtOAc/heptane to give the title compound as a yellow solid. Yield: 380 mg (63%). $^1$H NMR (399.961 MHz, CDCl$_3$) δ 8.22 (s, 1H), 7.64 (d, J=8.7 Hz, 2H), 7.53-7.42 (m, 4H), 6.72 (d, J=7.3 Hz, 1H), 6.61 (d, J=8.1 Hz, 1H), 5.48 (s, 2H), 4.41-4.01 (m, 3H), 3.43-3.25 (m, 2H), 1.97-1.74 (m, 4H), 1.42 (s, 9H). MS (ESI+) 553.3 (M+1H+)

e) 2-(4-Chlorophenyl)-6-({6-[(2R)-pyrrolidin-2-ylmethoxy]pyridin-2-yl}methyl)thieno[2,3-d]pyridazin-7(6H)-one tert-Butyl (2R)-2-{[(6-{[2-(4-chlorophenyl)-7-oxothieno[2,3-d]pyridazin-6(7H)-yl]methyl}pyridin-2-yl)oxy]methyl}pyrrolidine-1-carboxylate (380 mg, 0.69 mmol) was dissolved in 4M HCl in dioxane (1 mL) and stirred at ambient temperature for 3 h. The solvent was evaporated and the title compound was used directly in the next step. Yield: 310 mg (99%). $^1$H NMR (399.961 MHz, CDCl$_3$) δ 8.39 (s, 1H), 7.89 (t, J=8.0 Hz, 1H), 7.59 (d, J=8.5 Hz, 2H), 7.50 (s, 1H), 7.41 (d, J=8.7 Hz, 2H), 7.15 (d, J=7.5 Hz, 1H), 7.07 (d, J=8.5 Hz, 1H), 5.59 (d, J=14.9 Hz, 1H), 5.42 (d, J=14.9 Hz, 1H), 4.83-4.71 (m, 1H), 4.58-4.51 (m, 1H), 4.17-4.06 (m, 1H), 3.47-3.28 (m, 2H), 2.27-2.02 (m, 3H), 1.98-1.84 (m, 1H). MS (ESI+) 453.2 (M+1H+)

f) 2-(4-Chlorophenyl)-6-[(6-{[(2R)-1-methylpyrrolidin-2-yl]methoxy}pyridin-2-yl)methyl]thieno[2,3-d]pyridazin-7(6H)-one 2-(4-Chlorophenyl)-6-({6-[(2R)-pyrrolidin-2-ylmethoxy]pyridin-2-yl}methyl)thieno[2,3-d]pyridazin-7(6H)-one (0.340 g, 0.75 mmol), formaldehyde(aq.) 36% (0.23 mL, 2.25 mmol) and MacroPorous-triacetoxyborohydride (0.88 g, 2.25 mmol) were shaked in DCM/MeOH (1:1, 4 mL) at room temperature for 3 hours. The reaction mixture was filtrated, concentrated in vacuo and purified by flash chromatography using a gradient with EtOAc:MeOH:TEA (1:0.1:0.01) in n-heptane, which gave the product as an solid. Yield: 0.207 g (59%). $^1$H NMR (400 MHz, CDCl$_3$) δ 8.18 (s, 1H), 7.55-7.61 (m, 2H), 7.37-7.48 (m, 4H), 6.69 (d, 1H, J=7.27 Hz), 6.59 (d, 1H, J=8.26 Hz), 5.45 (s, 2H), 4.21-4.27 (m, 1H), 4.06-4.14 (m, 1H), 2.97-3.04 (m, 1H), 2.41-2.52 (m, 1H), 2.34 (s, 3H), 2.11-2.21 (m, 1H), 1.78-1.91 (m, 1H), 1.54-1.78 (m, 3H). $^{13}$C NMR (100 MHz, CDCl$_3$) δ 163.7, 157.4, 153.9, 152.3, 140.3, 139.2, 136.6, 136.0, 133.3, 131.4, 129.8, 128.2, 118.9, 114.3, 110.0, 68.3, 64.4, 57.9, 56.0, 41.8, 28.7, 23.1. MS (ESI+) 467.0 (M+1H$^+$).

Pharmacological Properties

MCHr1 Radioligand Binding

Assays were performed on membranes prepared from CHO-K1 cells expressing the human melanin concentrating hormone receptor 1 (hMCHr1, 5.45 μmol/mg protein; Euroscreen). Assays were performed in a 96-well plate format in a final reaction volume of 2001 per well. Each well contained 6 μg of membrane proteins diluted in binding buffer (50 mM Tris, 3 mM MgCl$_2$, 0.05% bovine serum albumin and the radioligand $^{125}$I-MCH (IM344 Amersham) was added to give 10 000 cpm (counts per minute) per well. Each well contained 2 μl of the appropriate concentration of competitive antagonist prepared in DMSO or in HOAc and left to stand at 30° C. for 60 minutes. Non-specific binding was determined as that remaining following incubation with 1 μM MCH (Melanin concentrating hormone, H-1482 Bachem). The reaction was terminated by transfer of the reaction to GF/A filters using a Micro96 Harvester (Skatron Instruments, Norway). Filters were washed with assay buffer. Radioligand retained on the filters was quantified using a 1450 Microbeta TRILUX (Wallac, Finland).

Non-specific binding was subtracted from all values determined. Maximum binding was that determined in the absence of any competitor following subtraction of the value determined for non-specific binding. Binding of compounds at various concentrations was plotted according to the equation $$y = A + ((B-A)/1 + ((C/x)^D)))$$

and IC$_{50}$ estimated where:

A is the bottom plateau of the curve i.e. the final minimum y value;

B is the top of the plateau of the curve i.e. the final maximum y value;

C is the x value at the middle of the curve; this represents the log EC$_{50}$ value when A+B=100;

D is the slope factor;

x is the original known x values;

y is the original known y values.

The compounds exemplified herein had IC$_{50}$ values of less than 150 nM in the abovementioned human MCHr1 binding assay. For instance, an IC$_{50}$ value of 26 nM was obtained for the compound of Example 1.

MCHr1 Functional Assay

Membranes expressing recombinant hMCHr1 (5.45 pmol/mg protein; Euroscreen) were prepared in assay buffer (50 mM HEPES, 100 mM NaCl, 5 mM MgCl$_2$, 1 mM EDTA, 200 μM DTT, 20 μM GDP (Sigma) containing 0.1 μg/ml BSA, pH7.4) before assay. The assays were performed using membranes at 6 μg/well in an assay volume of 200 μL and the appropriate concentrations of compounds prepared in DMSO or in HOAc. The reaction was started by addition of 0.056 nM [$^{35}$S]GTPγS (Specific activity >1000 Ci/mmol; Amersham) and an ED$_{80}$ concentration of MCH (determined for each membrane and each MCH batch). Non-specific binding was determined using 20 μM non-radiolabelled GTPγS. Plates were incubated for 45 min at 30° C. Free and bound GTPγS were separated by filtration binding using GF/B filter mats presoaked in wash buffer (50 mM Tris, 5 mM MgCl$_2$, 50 mM NaCl, pH 7.4) using a Micro96 cell harvester (Skatron Instruments) and the filters then dried at 50° C. before counting using a 1450 Microbeta TRILUX (Wallac).

Data are means±SD for experiments performed in triplicate. IC$_{50}$ values of antagonists were determined using non-linear regression analysis of concentration response curves using Activity Base. Compounds exemplified herein had IC$_{50}$ values of less than 200 nM in the abovementioned functional assay. For instance, an IC$_{50}$ value of 42 nM was obtained for the compound of Example 5.

hERG Activity hERG testing was performed using a modified version of the method described by Kiss et al., "High throughput ion-channel pharmacology: planar-array-based voltage clamp." Assay Drug Dev Technol., 2003, 1, 127-35. For instance, an IC$_{50}$ value of 6.5 μM was obtained for the compound of Example 1 in the abovementioned assay.

Diet Induced Obesity Model in Mouse

The utility of the compounds of the present invention in the treatment of obesity and related conditions is demonstrated by a decrease in body weight in cafeteria diet-induced obese mice. Female C57Bl/6J mice were given ad libitum access to calorie-dense 'cafeteria' diet (soft chocolate/cocoa-type pastry, chocolate, fatty cheese and nougat) and standard lab chow for 8-10 weeks until a body weight of 45-50 grams was achieved. Compounds to be tested were then administered perorally once daily for a minimum of 5 days, and the body weights of the mice monitored on a daily basis. During this period ad libitum access to calorie-dense 'cafeteria' diet and standard lab chow was maintained. Simultaneous assessment of adiposity was carried by means of DEXA imaging at baseline and termination of the study. Blood sampling was also carried out to assay changes in obesity-related plasma markers. Compounds of the invention induce significant decrease in body weigh in the abovementioned model, with the major effect being via a reduction in fat-mass.

Compounds of the invention have the advantage that they may be more potent, more selective (e.g. vs. ion channels such as hERG and/or vs. GPCR's related to MCHr1) more efficacious in vivo, be less toxic, produce fewer side effects, be more easily absorbed, be less metabolised and/or have a better pharmacokinetic profile than, or have other useful pharmacological or physicochemical properties over, compounds known in the prior art.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, and the like) cited in the present application is incorporated herein by reference in its entirety.

What is claimed is:

1. A compound of formula I

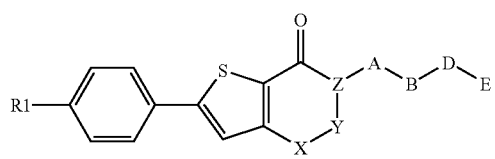

wherein:
X—Y—Z represents N=CH—N;
$R^1$ represents Cl, Br, F, $C_{1-3}$ alkyl (optionally substituted with one or more F), or alkoxy (optionally substituted with one or more F);
A represents a group —C($R^2$)$_2$—[(C$R^3$)$_2$]$_m$—, wherein $R^2$ and $R^3$, independently, represent H or $C_{1-3}$ alkyl, and wherein m is 0 or 1;
B represents phenyl, pyridinyl, pyrimidinyl, pyridazinyl, pyrazinyl, thiazolyl, or thiophenyl, each optionally substituted by one or more cyano, halo, $C_{1-3}$ alkyl (optionally substituted with OH, OMe and/or with one or more of F), or $C_{1-3}$ alkoxy (optionally substituted with one or more F or with OMe);
D represents a bond, —(CH$_2$)$_n$—, where n is 1 or 2, or —O(CH$_2$)$_p$—, where p is 0 to 2;
E represents one of the following:

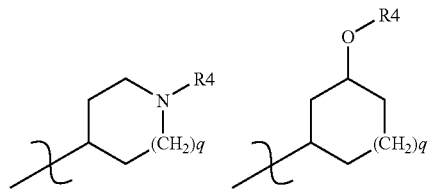

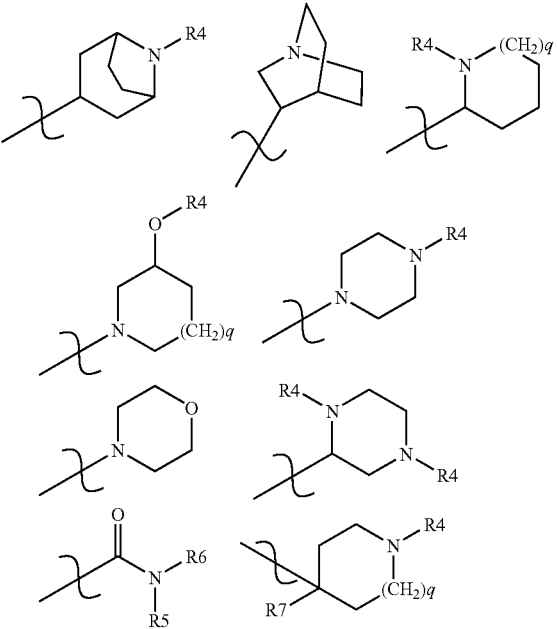

wherein:
$R^4$ represents H or $C_{1-5}$ alkyl, substituted with one or more F, OH, OCHF$_2$ or OCF$_3$;
$R^5$ and $R^6$, independently, represent H, $C_{1-5}$ alkyl, or $C_{3-6}$ cycloalkyl, or $R^5$ and $R^6$, together with the nitrogen to which they are attached, form a 5 or 6 membered ring optionally containing another nitrogen or oxygen atom;
q is 0 or 1; and
$R^7$ represents $C_{1-3}$ alkyl optionally substituted with one or more OH;

or a tautomer, optical isomer, or racemate thereof, as well as a pharmaceutically acceptable salt thereof.

2. A compound according to claim 1 wherein X—Y—Z represents N=CH—N.

3. A compound according to claim 1 wherein $R^1$ is Cl or CF$_3$.

4. A compound according to claim 1 wherein A is CH$_2$.

5. A compound according to claim 1 wherein B is 2,6-pyridinyl.

6. A compound according to claim 1 wherein B is phenyl.

7. A compound according to claim 1 wherein E is

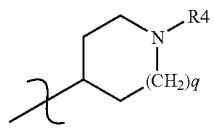

and $R^4$ represents H or methyl, and q is 1.

8. A compound according to claim 1 wherein B represents phenyl or pyridinyl, and D represents —O(CH$_2$)$_p$—, where p is 0 to 1.

9. A compound according to claim 1 wherein D is —O—.

10. A compound according to claim 1 wherein D is —O— and E is

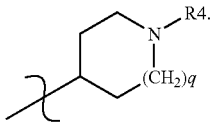

11. A compound according to claim 1 wherein:
X—Y—Z represents N═CH—N;
$R^1$ represents Cl, $C_{1-3}$ alkyl (optionally substituted with one or more F), or methoxy (optionally substituted with one or more F);
A represents $CH_2$;
B represents phenyl, pyridinyl, pyrimidinyl, pyridazinyl, pyrazinyl, thiazolyl, or thiophenyl, each optionally substituted by a cyano, a halo, or a hydroxymethyl;
D represents —O(CH$_2$)$_p$—, where p is 0 to 1; and
E represents:

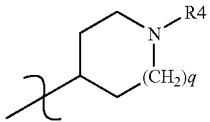

wherein $R^4$ represents H or methyl.

12. One or more of the following compounds:
6-(4-chlorophenyl)-3-(3-{[(3-endo)-8-methyl-8-azabicyclo [3.2.1]oct-3-yl]oxy}benzyl)thieno[3,2-d]pyrimidin-4(3H)-one;
6-(4-chlorophenyl)-3-{3-[(1-methylpiperidin-4-yl)oxy] benzyl}thieno[3,2-d]pyrimidin-4(3H)-one;
4-{2-[6-(4-chlorophenyl)-4-oxothieno[3,2-d]pyrimidin-3 (4H)-yl]ethyl}-N,N-diethylbenzamide;
6-(4-chlorophenyl)-3-[3-(4-methylpiperazin-1-yl)benzyl] thieno[3,2-d]pyrimidin-4(3H)-one;
6-(4-chlorophenyl)-3-{3-[(4-methylpiperazin-1-yl)methyl]benzyl}thieno[3,2-d]pyrimidin-4(3H)-one;
6-(4-chlorophenyl)-3-[3-(2-morpholin-4-yl-ethoxy)benzyl]thieno[3,2-d]pyrimidin-4(3H)-one;
6-(4-chlorophenyl)-3-(3-{[(3-exo)-8-methyl-8-azabicyclo [3.2.1]oct-3-yl]oxy}benzyl)thieno[3,2-d]pyrimidin-4(3H)-one;
6-(4-chlorophenyl)-3-{3-[(3R)-3-hydroxypyrrolidin-1-yl] benzyl}thieno[3,2-d]pyrimidin-4(3H)-one;
6-(4-chlorophenyl)-3-({6-[(1-methylpiperidin-4-yl)oxy] pyridin-2-yl}methyl)thieno[3,2-d]pyrimidin-4(3H)-one;
6-(4-chlorophenyl)-3-{3-[(1-methylpiperidin-3-yl)oxy] benzyl}thieno[3,2-d]pyrimidin-4(3H)-one;
6-(4-chlorophenyl)-3-{3-[(1-methylpiperidin-4-yl)methoxy]benzyl}thieno[3,2-d]pyrimidin-4(3H)-one;
6-(4-chlorophenyl)-3-[3-(piperidin-4-yloxy)benzyl] thieno[3,2-d]pyrimidin-4(3H)-one;
6-(4-chlorophenyl)-3-({2-[(1-methylpiperidin-4-yl)oxy] pyridin-4-yl}methyl)thieno[3,2-d]pyrimidin-4(3H)-one;
6-(4-chlorophenyl)-3-{3-[(1,4-dimethylpiperazin-2-yl) methoxy]benzyl}thieno[3,2-d]pyrimidin-4(3H)-one;
6-(4-chlorophenyl)-3-{3-[(1-methylpyrrolidin-3-yl)methoxy]benzyl}thieno[3,2-d]pyrimidin-4(3H)-one;
3-{3-[(3R)-1-azabicyclo [2.2.2]oct-3-yloxy]benzyl}-6-(4-chlorophenyl)thieno[3,2-d]pyrimidin-4(3H)-one;
6-(4-chlorophenyl)-3-{3-[(1-isopropylpiperidin-4-yl) oxy]benzyl}thieno[3,2-d]pyrimidin-4(3H)-one;
6-(4-chlorophenyl)-3-{3-[(1,3-dimethylpiperidin-3-yl) methoxy]benzyl}thieno[3,2-d]pyrimidin-4(3H)-one;
6-(4-chlorophenyl)-3-[(6-{[1-(2-hydroxyethyl)piperidin-4-yl]oxy}pyridin-2-yl)methyl]thieno[3,2-d]pyrimidin-4(3H)-one;
6-(4-chlorophenyl)-3-(3-{[(2S)-1-methylpyrrolidin-2-yl] methoxy}benzyl)thieno[3,2-d]pyrimidin-4(3H)-one; and as well as a tautomer, optical isomer, or racemate thereof, as well as a pharmaceutically acceptable salt thereof.

13. A pharmaceutical formulation comprising a compound of claim 1 and a pharmaceutically acceptable adjuvant, diluent, or carrier.

* * * * *